United States Patent
Mohammadi et al.

(10) Patent No.: US 12,156,832 B2
(45) Date of Patent: Dec. 3, 2024

(54) METHOD, AND SYSTEM FOR MULTI-LAYER COSMETIC PADS AND USE THEREOF

(71) Applicant: ELC Management LLC, Melville, NY (US)

(72) Inventors: Fatemeh Mohammadi, Hauppauge, NY (US); Tsung-Wei Robert Mou, Stony Brook, NY (US); Agostinho Martins, New Hyde Park, NY (US); Lisa Qu, Flushing, NY (US)

(73) Assignee: ELC MANAGEMENT LLC, Melville, NY (US)

( * ) Notice: Subject to any disclaimer, the term of this patent is extended or adjusted under 35 U.S.C. 154(b) by 618 days.

(21) Appl. No.: 17/142,252

(22) Filed: Jan. 6, 2021

(65) Prior Publication Data

US 2021/0205125 A1    Jul. 8, 2021

Related U.S. Application Data

(60) Provisional application No. 62/958,194, filed on Jan. 7, 2020.

(51) Int. Cl.
| | |
|---|---|
| *A61F 7/03* | (2006.01) |
| *A61F 7/00* | (2006.01) |
| *A61F 7/02* | (2006.01) |

(52) U.S. Cl.
CPC ...... *A61F 7/034* (2013.01); *A61F 2007/0003* (2013.01); *A61F 2007/0036* (2013.01);
(Continued)

(58) Field of Classification Search
CPC ............... A61F 7/034; A61F 2007/003; A61F 2007/0036; A61F 2007/0037;
(Continued)

(56) References Cited

U.S. PATENT DOCUMENTS

| | | |
|---|---|---|
| 4,747,841 A | 5/1988 | Kuratomi et al. |
| 5,658,583 A | 8/1997 | Zhang et al. |

(Continued)

FOREIGN PATENT DOCUMENTS

| | | |
|---|---|---|
| CN | 102186742 | 8/2013 |
| CN | 104398341 | 3/2015 |

(Continued)

OTHER PUBLICATIONS

PCT International Search Report; International Application No. PCT/US2021/012227; Completion Date: Apr. 27, 2021; Mailing Date: Apr. 27, 2021; 17.25.

(Continued)

*Primary Examiner* — Leslie A Lopez
*Assistant Examiner* — Timothy L Flynn
(74) *Attorney, Agent, or Firm* — Idris N. McKelvey

(57) ABSTRACT

A cosmetic pad, having a top layer constructed of nonwoven material, a bottom layer constructed in a manner to allow for ventilation through the bottom layer, and at least one heating element between the top layer and the bottom layer and methods for using the cosmetic pad and cosmetic agents therein are provided. A system for applying a cosmetic agent to a subject's skin, hair, hands, feet or face is also provided.

10 Claims, 26 Drawing Sheets

(52) U.S. Cl.
CPC .............. *A61F 2007/0037* (2013.01); *A61F 2007/0045* (2013.01); *A61F 2007/0052* (2013.01); *A61F 2007/0258* (2013.01); *A61F 2007/0263* (2013.01)

(58) Field of Classification Search
CPC ...... A61F 2007/0045; A61F 2007/0052; A61F 2007/0258; A61F 2007/0263
See application file for complete search history.

(56) References Cited

U.S. PATENT DOCUMENTS

| | | | |
|---|---|---|---|
| 5,975,074 | A | 11/1999 | Koiso et al. |
| 6,156,323 | A | 12/2000 | Verdicchio et al. |
| 6,158,427 | A | 12/2000 | McGuire et al. |
| 6,261,595 | B1 | 7/2001 | Stanley et al. |
| 6,306,431 | B1 | 10/2001 | Zhang et al. |
| 6,322,271 | B1 | 11/2001 | Girardot et al. |
| 6,406,206 | B1 | 6/2002 | Girardot et al. |
| 6,436,128 | B1 | 8/2002 | Usui |
| 6,453,648 | B1 | 9/2002 | Zhang et al. |
| 6,669,387 | B2 | 12/2003 | Gruenbacher et al. |
| 6,726,386 | B1 | 4/2004 | Gruenbacher et al. |
| 6,827,080 | B2 | 12/2004 | Fish et al. |
| 7,021,848 | B1 | 4/2006 | Gruenbacher et al. |
| 7,083,347 | B2 | 8/2006 | Marcotte et al. |
| 7,090,420 | B2 | 8/2006 | De La Poterie et al. |
| 7,108,440 | B1 | 9/2006 | Gruenbacher et al. |
| 7,211,070 | B2* | 5/2007 | Soroudi ............... A61K 9/0048 604/289 |
| 7,255,506 | B2 | 8/2007 | Gruenbacher et al. |
| 7,517,166 | B2 | 4/2009 | Keck |
| 7,575,384 | B2 | 8/2009 | Bauer et al. |
| 7,625,114 | B2 | 12/2009 | Suchan et al. |
| 7,650,995 | B2 | 1/2010 | Assie et al. |
| 7,722,782 | B2 | 5/2010 | Coffey et al. |
| 7,841,202 | B2 | 11/2010 | Madan et al. |
| 7,955,016 | B2 | 6/2011 | Gueret |
| 8,157,464 | B2 | 4/2012 | Prax |
| 8,220,451 | B2 | 7/2012 | Miwa et al. |
| 8,281,445 | B2 | 10/2012 | Adkins, Jr. et al. |
| 8,361,133 | B2 | 1/2013 | Cushman et al. |
| 8,372,130 | B2 | 2/2013 | Young |
| 8,506,539 | B2 | 8/2013 | Guillon et al. |
| 8,534,947 | B2 | 9/2013 | Prax |
| 8,689,387 | B2 | 4/2014 | Gundersen |
| 8,715,329 | B2 | 5/2014 | Robinson et al. |
| 8,839,782 | B2 | 9/2014 | Hess |
| 8,926,212 | B2 | 1/2015 | Gundersen |
| 8,945,072 | B2 | 2/2015 | Oda et al. |
| 9,004,059 | B2 | 4/2015 | Sesock et al. |
| 9,024,360 | B1 | 5/2015 | Huffer et al. |
| 9,079,208 | B2 | 7/2015 | Gundersen |
| 9,161,603 | B2 | 10/2015 | Gundersen |
| 9,185,961 | B2 | 11/2015 | Gundersen |
| 9,278,796 | B2 | 3/2016 | Huffer et al. |
| 9,278,800 | B2 | 3/2016 | Seo et al. |
| 2002/0020407 | A1 | 2/2002 | Wohland et al. |
| 2004/0042965 | A1 | 3/2004 | Usui et al. |
| 2004/0109720 | A1 | 6/2004 | Gruenbacher et al. |
| 2004/0223802 | A1 | 11/2004 | Bergey et al. |
| 2005/0229343 | A1 | 10/2005 | Dammen et al. |
| 2006/0210752 | A1 | 9/2006 | Ota et al. |
| 2006/0217790 | A1* | 9/2006 | Ota .................... A61F 7/032 607/114 |
| 2006/0246118 | A1 | 11/2006 | Gueret |
| 2006/0251686 | A1 | 11/2006 | Gueret |
| 2006/0289565 | A1 | 12/2006 | Manzo et al. |
| 2007/0034202 | A1 | 2/2007 | Pumphrey et al. |
| 2007/0223988 | A1 | 9/2007 | Gruenbacher et al. |
| 2008/0050690 | A1 | 2/2008 | Madan et al. |
| 2008/0097356 | A1 | 4/2008 | Donovan |
| 2008/0097358 | A1 | 4/2008 | Donovan et al. |
| 2008/0206165 | A1 | 8/2008 | Mitra et al. |
| 2008/0283038 | A1 | 11/2008 | Dodo |
| 2009/0112231 | A1 | 4/2009 | Luizzi |
| 2009/0118684 | A1 | 5/2009 | Da Silva et al. |
| 2009/0208542 | A1 | 8/2009 | Barrow |
| 2009/0208592 | A1 | 8/2009 | Barrow |
| 2009/0209600 | A1 | 8/2009 | Miner et al. |
| 2009/0264971 | A1 | 10/2009 | Wickstead |
| 2010/0146849 | A1 | 6/2010 | Coffey et al. |
| 2010/0163011 | A1 | 7/2010 | Tinker et al. |
| 2010/0241200 | A1 | 9/2010 | Bruder et al. |
| 2011/0046581 | A1 | 2/2011 | Linder |
| 2011/0073099 | A1 | 3/2011 | Madan et al. |
| 2011/0232565 | A1 | 9/2011 | Gundersen |
| 2012/0145189 | A1 | 6/2012 | Knopow et al. |
| 2013/0174835 | A1 | 7/2013 | Tinker et al. |
| 2013/0345649 | A1 | 12/2013 | Stockley, III et al. |
| 2014/0058340 | A1 | 2/2014 | Guillon et al. |
| 2014/0208532 | A1 | 7/2014 | Gundersen |
| 2014/0303698 | A1 | 10/2014 | Benyaminpour et al. |
| 2015/0297394 | A1* | 10/2015 | Young .................. A61F 7/0097 607/96 |
| 2015/0335132 | A1 | 11/2015 | Hall |
| 2016/0114143 | A1 | 4/2016 | Kowalewski et al. |
| 2016/0158510 | A1 | 6/2016 | Casasanta, III et al. |
| 2016/0279245 | A1 | 9/2016 | Hull et al. |
| 2016/0310716 | A1 | 10/2016 | Guillon et al. |
| 2017/0021586 | A1 | 1/2017 | Huffer et al. |
| 2020/0214423 | A1* | 7/2020 | Samangooie ....... A61M 35/006 |

FOREIGN PATENT DOCUMENTS

| | | |
|---|---|---|
| CN | 102421399 | 4/2015 |
| CN | 102361608 | 7/2015 |
| CN | 103140195 | 9/2015 |
| CN | 103889267 | 9/2016 |
| CN | 105997335 | 12/2016 |
| EP | 1557146 A1 | 7/2005 |
| EP | 2326569 | 11/2012 |
| EP | 2403445 | 1/2013 |
| EP | 2403446 | 12/2014 |
| EP | 2810627 A1 | 12/2014 |
| EP | 2621431 | 5/2015 |
| EP | 2747595 | 12/2015 |
| FR | 2876358 | 4/2006 |
| FR | 2967756 | 5/2012 |
| FR | 2967757 | 5/2012 |
| GB | 2515112 | 12/2014 |
| JP | 2012130484 | 7/2012 |
| JP | 2012519531 | 8/2012 |
| JP | 2012519684 | 8/2012 |
| JP | 5121634 | 1/2013 |
| JP | 2014504195 | 2/2014 |
| JP | 2014524322 | 9/2014 |
| JP | 2015084949 | 5/2015 |
| JP | 5890179 | 3/2016 |
| JP | 5975074 | 8/2016 |
| JP | 6158427 | 7/2017 |
| JP | 6453648 | 1/2019 |
| JP | 6554892 | 8/2019 |
| KR | 10-2011-0066916 | 6/2011 |
| KR | 10-2012-0002983 | 1/2012 |
| KR | 10-2012-0002986 | 1/2012 |
| KR | 10-1225396 | 1/2013 |
| KR | 10-2013-0132785 | 12/2013 |
| KR | 10-2014-0086956 | 7/2014 |
| KR | 10-1651109 | 9/2016 |
| KR | 20-2018-0001824 U | 6/2018 |
| WO | WO-2003/086167 | 10/2003 |
| WO | WO-2007/011239 | 1/2007 |
| WO | WO-2008/048603 | 4/2008 |
| WO | WO-2008/060162 | 5/2008 |
| WO | WO-2009/028951 | 3/2009 |
| WO | WO-2009/028952 | 3/2009 |

OTHER PUBLICATIONS

PCT Written Opinion of the International Searching Authority; International Application No. PCT/US2021/012227; Completion Date: Apr. 27, 2021; Mailing Date: Apr. 27, 2021; 17.25.

(56) References Cited

OTHER PUBLICATIONS

Taiwan Search Report from TW Application No. 110100626; Date: Nov. 12, 2021; 17.25.
Supplementary European Search Report; EP Application No. 21738448; Completion Date: Apr. 28, 2023; 17.25.

* cited by examiner

METHOD, AND SYSTEM FOR MULTI-LAYER COSMETIC PADS AND USE THEREOF

FIELD

The present disclosure relates generally to methods, and systems for providing multi-layer pads, more particularly, multi-layer pads for cosmetic or dermatological use.

BACKGROUND

Existing personal-care pads or pouches on the market are designed as an applicator or a carrier/formulation that may be applied on the human skin. For example, facial cleansing pads or pillows are commercially available on the market. As another example, travel size or single-dosed personal care formulations are also available on the market. However, currently available products do not combine the benefits of storing and applying the formulation to the skin in one convenient package. Further, current products do not include exfoliation and self-heating elements in such designs and applications.

SUMMARY

Embodiments herein provide a cosmetic pad, and methods for using the cosmetic pad. The cosmetic pad comprises a top layer constructed of non-woven material, a bottom layer constructed in a manner to allow for ventilation through the bottom layer and at least one heating element between the top layer and the bottom layer. The at least one heating element is an exothermic heating source and is activated by exposing the exothermic heating source to air.

The cosmetic pad may further comprise an air-diffusing layer in between the top layer and the bottom layer, a formulation layer having one or more products in between a formulation top layer and a formulation bottom layer. One or more products are present as an emulsion, a gel, a lotion, a cream, a serum, or a suspension. The cosmetic pad is inside a sealed package. The bottom layer of the cosmetic pad comprises one or more apertures for ventilation and the bottom layer further comprises a breathable material for ventilation. The at least one heating element is a single-phase or a dual-phase heating element. The cosmetic pad further comprises a finger pocket in between the top layer and the bottom layer. The one or more product comprises a cosmetic agent or dermatologic agent and may be a peptide, small molecule, protein, plant or fruit extract, vitamin, oil, organic oil, protein or mixtures thereof.

A method for applying one or more cosmetic products is provided. The method comprising applying the cosmetic pad to one or more areas of skin by inserting one or more fingers into the finger pocket of the cosmetic pad. A method of using the cosmetic pad is also disclosed wherein, the method comprises opening the cosmetic pad, sliding at least one finger into the cosmetic pad, and releasing a formulation housed in the cosmetic pad, wherein the formulation comprises one or more cosmetic or dermatologic agent and the cosmetic pad is applied in areas of skin, body or hair in an effective amount.

A system for applying a cosmetic or dermatologic agent to a subject's skin, hands, feet, hair or face using the cosmetic pad is also provided. The cosmetic pad is attached to a device or an applicator and at least one formulation comprising a cosmetic agent or dermatologic agent is housed within the cosmetic pad. The system may be a hand treatment or a feet treatment.

DETAILED DESCRIPTION

Figure 1A:
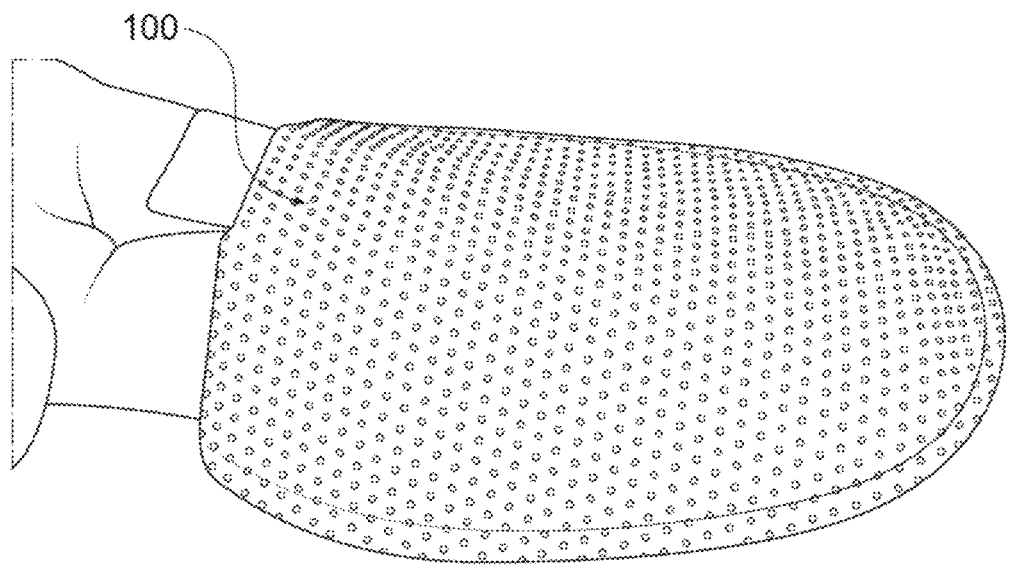
FIG. 1A shows a skin contact side of a cosmetic pad, according to an embodiment herein.

To facilitate an understanding of this disclosure, several terms are defined below. Terms defined herein have meanings as commonly understood by a person of ordinary skill in the areas relevant to the present disclosure. Terms such as "a", "an" and "the" are not intended to refer to only a singular entity but include the general class of which a specific example may be used for illustration. The terminology herein is used to describe specific embodiments of the disclosure, but their usage does not delimit the disclosure, except as outlined in the claims.

As used herein, a "cosmetic agent" means cosmetic agents suitable for topical application on mammalian keratinous tissue. The cosmetic agent may be a substance that aids in the cleansing or enhancement or protection of the appearance (e.g., color, texture, look, feel, etc.) or odor of a subject's skin, body or hair. The cosmetic agent may change the underlying structure of the skin or hair.

A "subject" refers to any mammal, preferably a human.

As used herein, the term "topical" refers to administration of an agent or agents (e.g., cosmetic, vitamin, etc.) on the skin.

"Transdermal" refers to the delivery of an agent (e.g., cosmetic, dermatological, vitamin, etc.) through the skin (e.g., so that at least some portion of the population of molecules reaches underlying layers of the skin).

Except in operating and comparative examples, or where otherwise explicitly indicated, all numbers in this description indicating amounts or ratios of material or conditions of reaction, physical properties of materials and/or use are to be understood as modified by the word "about". All amounts are presented as percentages by weight of the final cosmetic agent, unless otherwise specified.

The embodiments of the present disclosure provide a self-heating, on-the-go cosmetic pad comprising a pouch. The pouch may be preloaded with a treatment product comprising a cosmetic or a dermatologic agent. The cosmetic or dermatologic agent may be present as a formulation.

In one aspect of the present disclosure, the cosmetic pad is constructed with layer(s) of exfoliating substrate and a self-heating source to enhance treatment efficacy and provide faster results compare to the conventional skincare products. The pad may provide exfoliating benefits in some embodiments. The pad may provide cleansing, skin brightening, lightening or whitening benefits in other embodiments. The cosmetic pad may be used as a skin, body or hair treatment system.

A unique skin care system is provided herein, the system comprising as a single dose pad, constructed with a skin contact layer, a preloaded compartment with a treatment product comprising a formulation of cosmetic or dermatologic agent, and a self-heating source. Self-heating sources may be any of the following type, air activated, water-inorganic salt mixture, water-polyalcohol mixture, or battery powered heating paper/substrate. In one embodiment, the system may comprise more than one pre-loaded compartment and thus include more than one formulation, respectively. The system further comprises a device or an applicator attached to the pad.

A method for applying one or more formulation comprising a cosmetic or dermatologic agent is provided herein. The method comprising applying a cosmetic pad having a top layer constructed of non-woven material, a bottom layer constructed in a manner to allow for ventilation through the bottom layer and at least one heating element between the top layer and the bottom layer. A method of using the cosmetic pad is also disclosed wherein, the method comprises opening the cosmetic pad, sliding at least one finger into the cosmetic pad, and releasing a formulation housed in the cosmetic pad, wherein the formulation comprises one or more cosmetic or dermatologic agent and the cosmetic pad is applied in areas of skin, body or hair in an effective amount.

In embodiments, the formulation housed within the cosmetic pad may be used for whitening, brightening, anti-aging, acne, smoothening, moisturization, hyperpigmentation, depilatory (hair removal), cellulite, stretch marks, spider veins, scalp treatment, hair growth, and other cosmetic or dermatologic benefits for the face, body, or hair. In specific embodiments, the treatment products are present as a formulation comprising cosmetic agents, dermal fillers, peptides, vitamins, small molecules, large molecules, proteins, bio actives, alone or in combinations or in mixtures. All forms of the formulation are contemplated to be within the scope of the present disclosure, including encapsulated, unencapsulated or impregnated forms useful for application of such cosmetic or dermatologic agents and may be in the form of an emulsion, a gel, a lotion, a cream, a serum, or a suspension.

FIG. 1A shows a skin contact side of a cosmetic pad 100 and the top view of the cosmetic pad 100, according to an embodiment herein. The cosmetic pad comprises a top layer, a bottom layer and at least one heating element between the top layer and the bottom layer. The skin contact side may be constructed from non-woven material or any other suitable substrate. In embodiments where exfoliation is desired, the material may be an exfoliating substrate, such as cotton, wool, synthetic and/or natural fibers, or any suitable materials. In embodiments where skin smoothening is desired, the material may be a substrate suitable for such a purpose. In embodiments, where cleansing is required, the material may be a substrate suitable for such a purpose. In embodiments, where make-up is required, the material may be a substrate suitable for such a purpose. Exemplary materials include, without limiting, PP, polyethylene terephthalate (PET) or PE non-woven material having a melting point in the range from about 80° C. to about 300° C. In some embodiments, the thickness of the material ranges from about 1 millimeter (mm) to 10 centimeter (cm), and a relative density ranging from 0.01 grams/centimeter$^3$ (g/cm$^3$) to 20 g/cm$^3$.

Figure 1B:
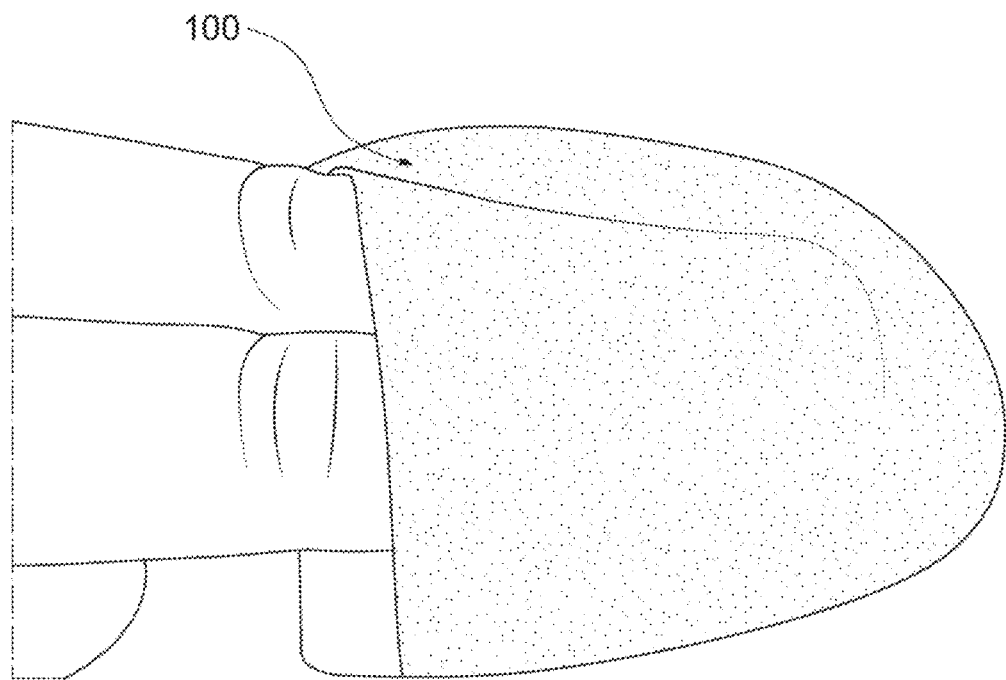
FIG. 1B shows a ventilating side of the cosmetic pad shown in FIG. 1A.
Figure 1C:
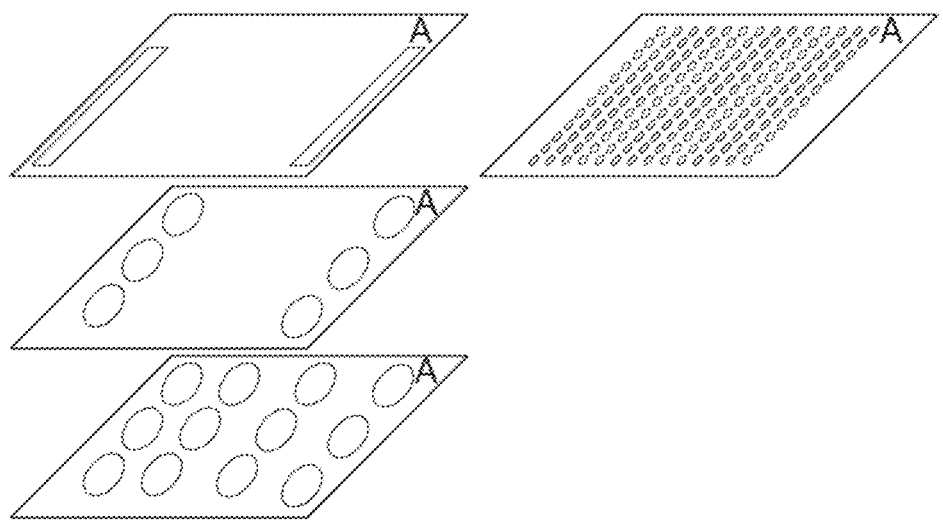
FIG. 1C shows exemplary arrangements of ventilation for the ventilating side of the skin cosmetic pad shown in FIG. 1B.

FIG. 1B shows a ventilating side or the bottom view that comprises a ventilating layer A of the cosmetic pad 100. The ventilating side may include a film with ventilating cutouts, as shown in FIG. 1C. In alternative embodiments, the ventilating side of the cosmetic pad may be constructed of a breathable and air permeable material, such as mesh, to allow for proper ventilation and adequate airflow without cutouts or other ventilating apertures. In some embodiments, the ventilating side of the cosmetic pad is coated with an appropriate polymer or co-polymers. Exemplary coating includes ethylene acetate, ethylene vinyl acetate, vinyl acetate. In embodiments, the ventilation side of the cosmetic pad may be made of material having a melting point in the range from about 80° C. to about 600° C. Exemplary materials include, without limiting, PP, polyethylene terephthalate (PET) or PE non-woven material. In some embodiments, the thickness of the material ranges from about 1 millimeter (mm) to about 1 centimeter (cm), and a relative density ranging from about 0.01 grams/centimeter$^3$ (g/cm$^3$) to about 20 g/cm$^3$. In some embodiments, the material may be pigmented. In a preferred embodiment, the ventilating side may have many ventilating apertures as shown in FIG. 1C. Such apertures may be of same or different sizes.

FIG. 1C shows an exemplary arrangement of ventilation apertures that are present in the ventilating layer A (i.e., the bottom view) of the skin cosmetic pad 100. As shown, the ventilating apertures may vary in number, shape, size, and arrangement on the ventilating layer. In some embodiments, the apertures may be pigmented. In other embodiments, the apertures may be textured. A finger pocket is present between the bottom layer A (201) and the layer E (203).

Figure 1D:
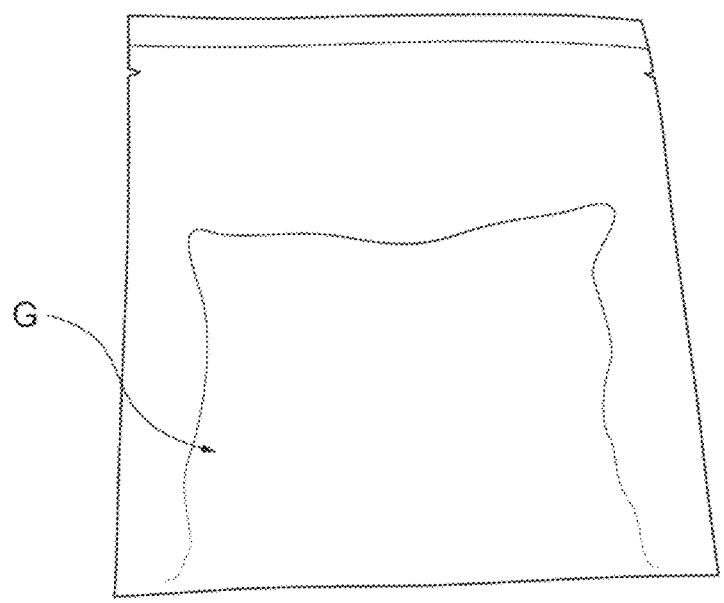
FIG. 1D shows an exemplary outside view of the cosmetic pad.

FIG. 1D shows an exemplary outside view of the cosmetic pad 100. The skin cosmetic pad 100 is housed in a moisture barrier bag layer G. The moisture barrier bag layer blocks moisture and air from the cosmetic pad 100. In one embodiment, the layer G is made of laminated polyester foil, polyethylene or polyester.

Figure 2A:
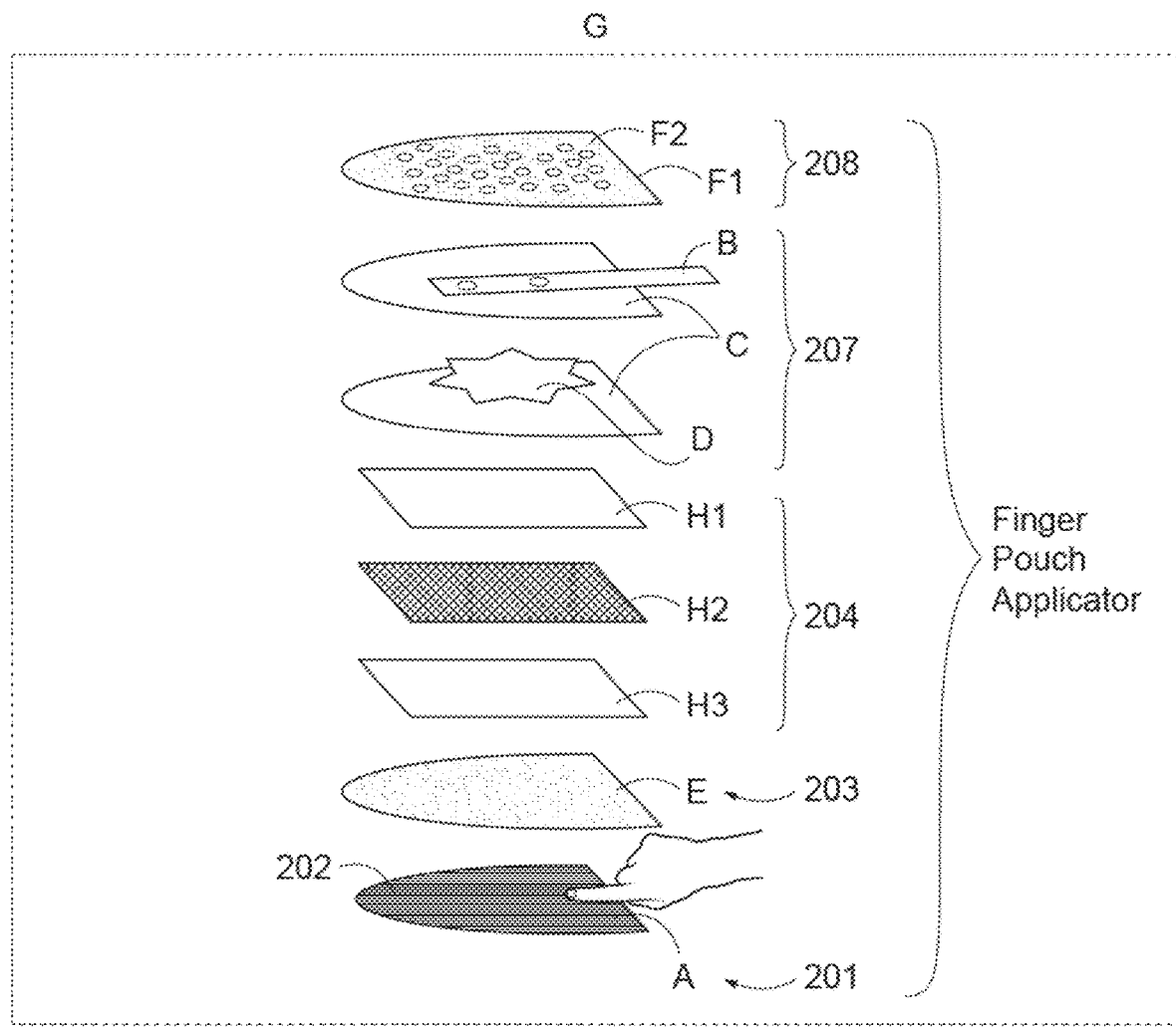
FIG. 2A shows an exploded view of the cosmetic pad of FIG. 1A and FIG. 1B.

FIG. 2A shows an exploded view of the various layers of a cosmetic pad, according to one embodiment herein.

As shown in FIG. 2A, layer A is the ventilating layer 201, which may include ventilating apertures 202 in some embodiments. As previously noted, ventilating layer 201 may be constructed of a film material or may be coated. This layer also serves to provide a layering material to create a pocket to insert fingers into and secure the pad during use or application. Based on the desired aesthetic feel and product design of the pad, a rigid or soft material may be selected. Exemplary suitable materials for the film layer are polypropylene (PP) and polyethylene (PE) films with aluminum, such as Ceramis® available from Amcor. Alternatively, the ventilating layer 201 may be constructed from a naturally ventilating material, such as mesh to allow for airflow without having specific cutouts. In some embodiments, the ventilating layer A may be constructed using a film material.

In some embodiments, the material may be coated using, for example, ethylene acetate, ethylene vinyl acetate, vinyl acetate etc. In some embodiments, the layer A has a thickness ranging from about 0.1 millimeter (mm) to about 1 centimeter (cm), weight ranging from about 0.1 grams/meter$^2$ (g/m$^2$) to about 200 g/m$^2$ and having a melting point in the range from about 100° C. to about 300° C.

Layer E functions as an air-diffusing layer 203, a circulation layer, or an insulation layer. Air-diffusing layer 203 may be constructed from, for example, but not limited to, PP, polyethylene terephthalate (PET), or PE nonwovens having a thickness ranging from about 0.1 millimeter (mm) to about 1 centimeter (cm), weight ranging from about 0.1 grams/meter$^2$ (g/m$^2$) to about 200 g/m$^2$ and a melting point in the range from about 100° C. to about 300° C. For example, nonwoven materials are available from Fibertex®. The air diffusing layer 203 is present between the bottom layer of the cosmetic pad and the top layer of the cosmetic pad. Specifically, the air diffusing layer 204 is present between the bottom layer of the cosmetic pad and the heating layer 204.

Layer 204, also shown as layer H is the heating layer having at least one heating element and is comprised of layers H1, H2 and H3. Heating layer 204 is further delineated below in FIG. 2B, which shows the components H1, H2 and H3 of the layer H. Components H1, H2, and H3 of the heating layer 204 are sealed together using an appropriate seal, such as a heat seal (i.e., using heat to seal the layers). In some embodiments, more than three components may be included. In some embodiments, two or even one component may be included. All such combinations are considered to be within the scope of the present disclosure.

According to an exemplary embodiment, H1 may be constructed of a breathable, flexible and air permeable material, such as polyolefin film, PP, polyethylene terephthalate (PET) or PE non-woven material. H2 is a heating engine, which may be constructed using element such as carbon, zinc, PTFG, cellulose, water and salt. An exemplary heating element that may be used in cosmetic pads herein is the Exothermix® heater, which is commercially available from Rechargeable Battery Corporation. H3 may be made of any material that is breathable and that provides ventilation and air circulation, such as non-woven material, polyolefin film, PP, polyethylene terephthalate (PET) or PE non-woven material.

According to an embodiment of the present disclosure, it is contemplated that the cosmetic pad 100 comprises at least one heating element 204. In another embodiment, the cosmetic pad 100 may include more than one heating element 204. In embodiments that comprise more than one heating element, it is contemplated that such heating elements may be arranged in any manner, for example, overlapping, non-overlapping, portions that are overlapping while other portions are non-overlapping etc. The heating element may provide a single-phase heating or a dual phase heating.

The heating element 204 may generate heat from about 5 seconds to about 5 hours. In embodiments, the heating element may generate heat from about 5 seconds to about 30 minutes, from about 5 seconds to about 45 minutes, from about 5 seconds to about 60 minutes. In some embodiments, the heating element may generate heat from about 35° C. to about 70° C. In an embodiment, the heating elements generates heat from about 37° C. to about 50° C., within about 1 second to about 30 minutes, within about 1 second to about 45 minutes.

In FIG. 2A, Layer C, 207 depicts the housing for the formulation, which is the formulation layer C, 207. The formulation layer C comprises at least one formulation-top layer and at least one formulation-bottom layer, wherein both the formulation-top and the formulation-bottom layer (s) are sealed together using a heat seal, adhesive or any appropriate sealing mechanism. Depending on the form and viscosity of the formulation comprising the cosmetic agent, the formulation may be housed in a free form in a chamber or inside of an enclosed layer as shown in D, having one or more openings that may be found on the formulation-top layer of C, which constitute means for the formulation to pass through. If the formula is a watery lotion or thinner in viscosity, the additional formulation layer is needed to ensure even distribution of formulation within the chamber. If formulation is thicker than a light lotion, then the formulation may be in a free form and may have more than one opening to be able to pass through the formulation-layer(s) while being used. In alternate embodiments, the formulation may be impregnated in the layer C, such that the formulation may be found within the formulation-top layer or the formulation-bottom layer or both. In some embodiments, multiple formulations may be housed in the layer. In specific embodiments, multiple formulations may be either housed or impregnated in layer C.

As an example, the formulation may be housed in a formulation layer(s) constructed from PET, PP or PE nonwovens similar to those for air-diffusing layer 203, having a thickness ranging from 1 millimeter (mm) to 1 centimeter (cm), and weight ranging from 1 g/m² to 200 g/m².

A pull tab B is shown in FIG. 2A. The pull tab B is connected to layer C (includes both formulation-top and formulation-bottom layers) using heat sealing, adhesive or an appropriate tearable mechanism. Upon releasing the pull tab via a pulling or tearing mechanism, the formulation present in the layer C (includes both formulation-top and formulation-bottom layers) will pass through the opening (present in the formulation-top layer of C) and thus, the formulation will become available for use. In some embodiment, more than one opening is contemplated. If the formulation is thick or highly viscous, many holes/openings may be used to allow the formulation to pass through and such holes may be arranged in any manner. Any formulation comprising a cosmetic or dermatologic agent may be housed in layer C (includes both formulation-top and formulation-bottom layers). The formulation may have viscosity ranging from about 1000 centipoise to about 1,00,000 centipose units, including any ranges and sub-ranges therein.

Layer F1 is a skin contact layer 208, which may be constructed from PE, PET or PP nonwovens, such as Sawabond® nonwovens available from Sandler, or any other suitable nonwovens. As an example, the skin contact layer 208 may be constructed of a blend of wood pulp and polyester having acrylic dots F2 on the surface for the purpose of exfoliation, cleansing, skin whitening, skin smoothening, acne removal, make application etc. An exemplary material for skin contact layer 208 is the Aquadim® available from Fibertex Nonwovens.

The entire cosmetic pad 100 may be housed within a moisture barrier bag layer G. The moisture barrier bag layer blocks moisture and air from the cosmetic pad 100. In one embodiment, the layer G is made of laminated polyester foil, or polyethylene or polyester.

It is to be understood that the arrangement of the layers shown and described in the context of FIG. 2A are exemplary and that the layers may be arranged in other order, or may include additional layers, or exclude certain layers.

Figure 2B:
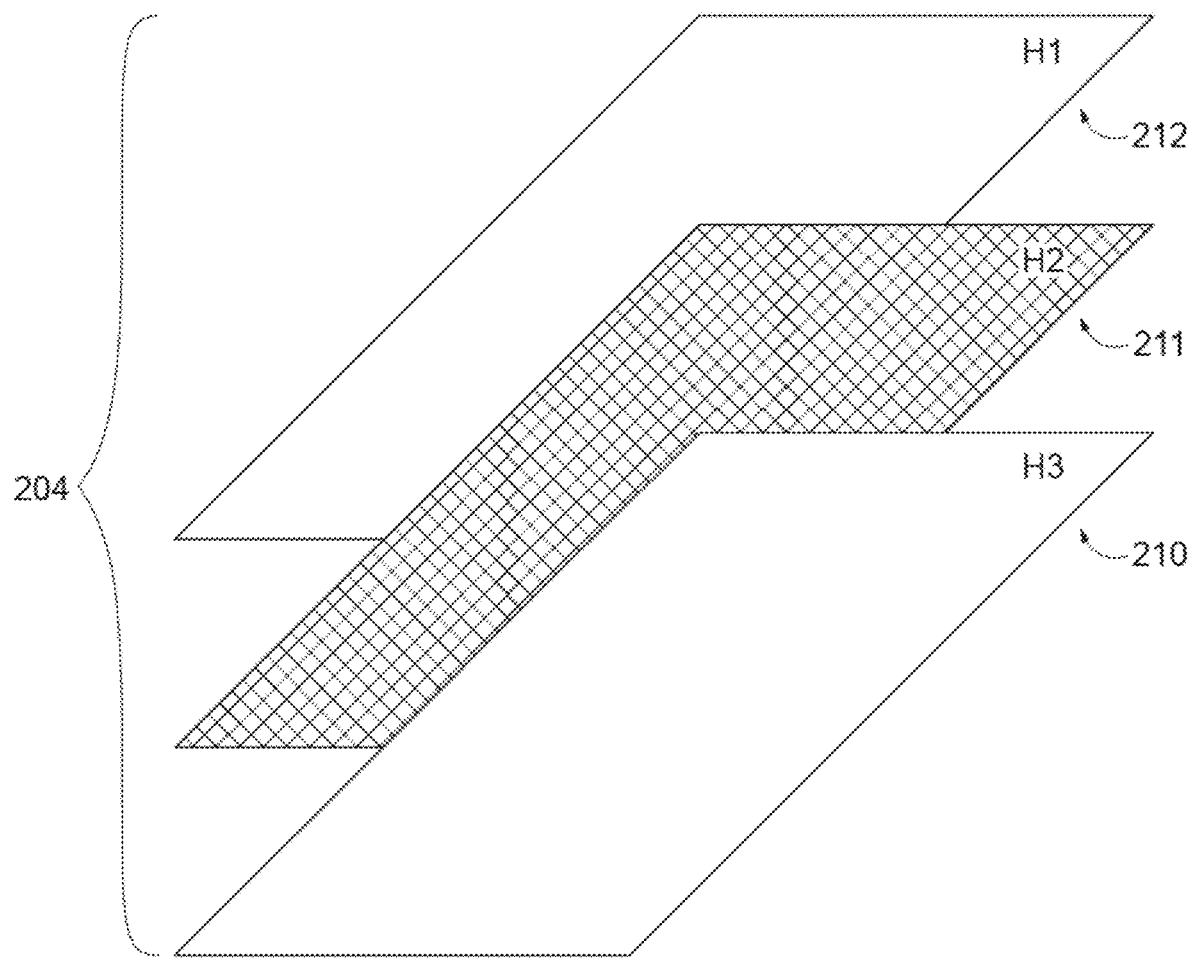
FIG. 2B shows an exploded view of layer C of FIG. 2A.

FIG. 2B shows an exploded view of the heating layer 204, according to an embodiment of the present disclosure.

According to an embodiment shown in FIG. 2B, the heating element H includes layers H1-H3, which may be made of non-woven material that allows air to circulate once the moisture barrier bag layer G (shown in FIG. 2A) is opened. In some embodiments, more than one heating source is contemplated. In some embodiments, the heating layer 204 may be more than three layers, and all combinations of layers and heating elements are considered to be within the scope of the present disclosure.

Alternatively, in a different embodiment, the layer H1 and layer H3 shown in FIG. 2B may be barrier layers, respectively. Layer 210 and layer 212 may serve as a moisture barrier or air barrier layer to prevent premature exposure and activation of the heating element. One or both of barrier layers 210 and 212 may be a film layer constructed from aluminum or any other suitable material. Barrier layer 210 may include a pull tab (205, not shown herein) which reveals an aperture, (for example, aperture K, not shown herein), when pulled to expose the self-heating mechanism to initiate an exothermic reaction and allow for heat activation, for example, exposure to air for air activated heating mechanisms. Also, in the alternative embodiment, positioned in between barrier layers 210 and 212 is layer is H2, which comprises a heating element 211. The alternative embodiment is also shown in FIG. 5B.

Heating element 211 may include at least one self-heating source, which may be an air activated heating source, a water-inorganic salt mixture, a water-polyalcohol mixture, or battery powered heating paper/substrate. Layers 210, 211, and 212 together form heating layer 204, and these layers may be provided as a single unit to be assembled as part of the cosmetic pad 100.

Heating layer 204 may include more or fewer components than shown and described in FIG. 2B. For example, heating layer 204 may include multiple heating sources, or fewer or more barrier layers.

Figure 3:
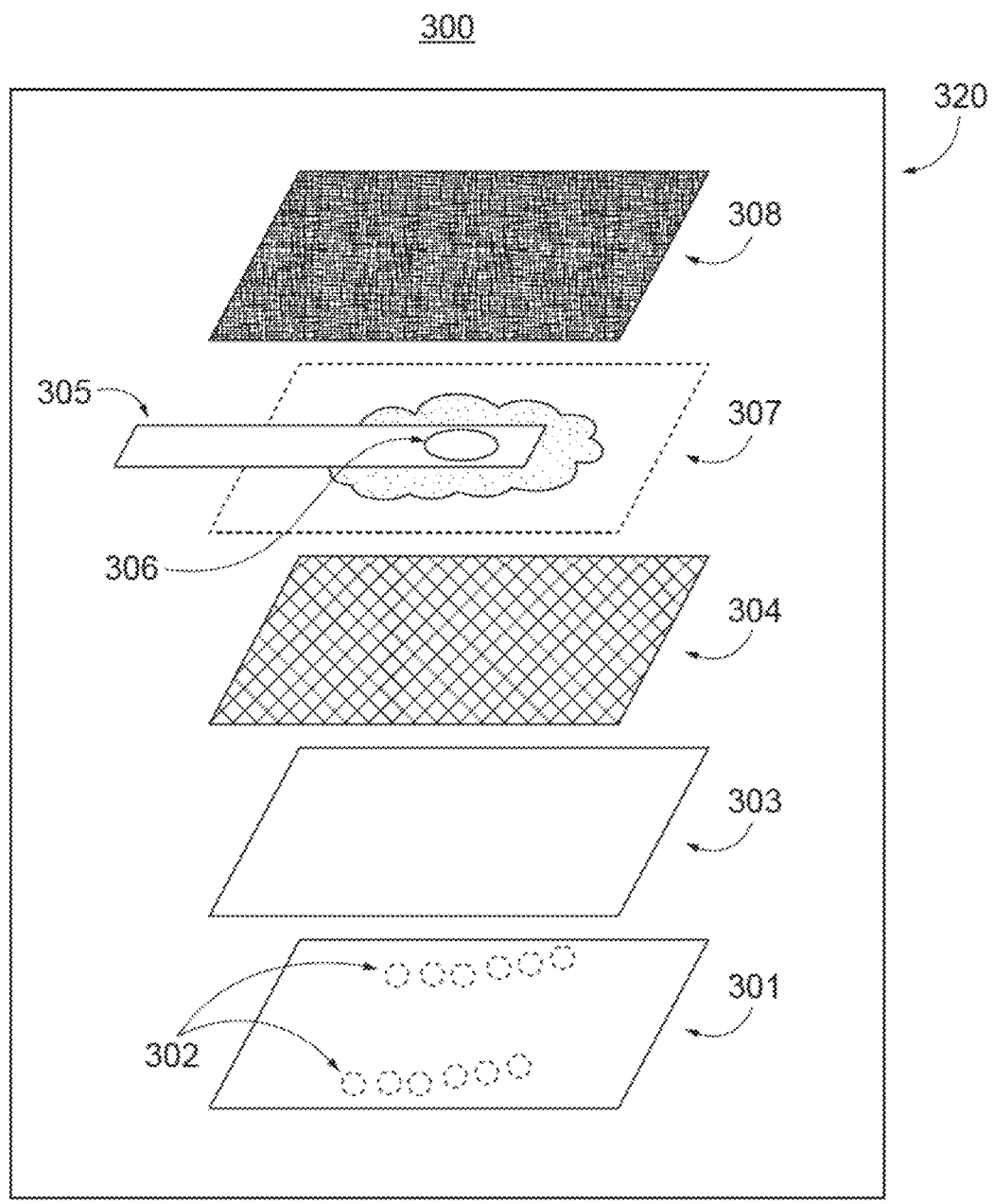
FIG. 3 shows an exemplary cosmetic pad, according to another embodiment herein.

FIG. 3 shows an exemplary cosmetic pad 300 according an embodiment of the present disclosure. As shown, the ventilating layer is 301, which may include ventilating apertures 302 in some embodiments. Ventilating layer 301 may be constructed of a film material or non-woven material and may include ventilating apertures 302. In a variation, the ventilating layer may be constructed of a breathable/ventilating material to allow for airflow within the cosmetic pad 300 without having specific cutouts/apertures. Layer 301 may also serve to create a pocket to insert fingers into and secure the pad during application or use.

Exemplary suitable materials for this film layer are polypropylene (PP) and polyethylene (PE) films with aluminum, such as Ceramis® available from Amcor. Layer 303 function as an air-diffusing layer, a circulation layer, or an insulation layer. Air-diffusing layer 303 may be constructed from, for example, but not limited to, PP, PET, or PE nonwovens having a thickness ranging from 1 millimeter (mm) to 10 centimeter (cm), and weight ranging from 0.1 grams/meter² (g/m²) to 200 g/m². For example, nonwoven materials available from Fibertex® may be utilized. Layer 304 is the heating layer, which includes a self-heating element. An exemplary self-heating heating element that may be used in cosmetic pads of the present disclosure is an exothermic heater, Exothermix® heater commercially available from Rechargeable Battery Corporation.

Layer 307 is formulation layer. The formulation may be housed in a free form in a chamber or inside an enclosed layer having means for the formulation to pass through, such as a pull tab 305 that will expose aperture 306 to allow for the formulation/product to flow through. In some embodiments, the formulation/product may be an aqueous solution, ointment for use, cream, foam, milky lotion, or nutritive cosmetic water, softening cosmetic water, milky liquid, base for makeup, essence, soap, a cleaning solution, sunscreen cream or oil, suspension, emulsion, gel, paste, lotion, powder, surfactant containing cleaning, oil, powder, foundation, emulsion, foundation, or wax foundation or a combination thereof. For example, the formulation may be housed in a layer constructed from PP or PE nonwovens similar to those for air-diffusing layer 203, having a thickness ranging from 1 millimeter (mm) to about 1 centimeter(cm), and weight ranging from 1 g/m² to about 200 g/m². Layer 308 is the skin contact layer, which may be constructed from PE or PP nonwovens, such as Sawabond® nonwovens available from Sandler, or any other suitable nonwovens. The cosmetic pad 300 may be provided in a sealed package 320 that is air-tight, which when opened allows for air flow through the various layers of the cosmetic pad 300 and activating an exothermic heating element 304. Advantageously, the sealed package 320 will keep the skin contact side clean and hygienic until the point of use by consumer. The sealed package 320 may be made of materials that are not gas permeable to prevent unintentional or premature activation of the self-heating element 304.

Figure 4:
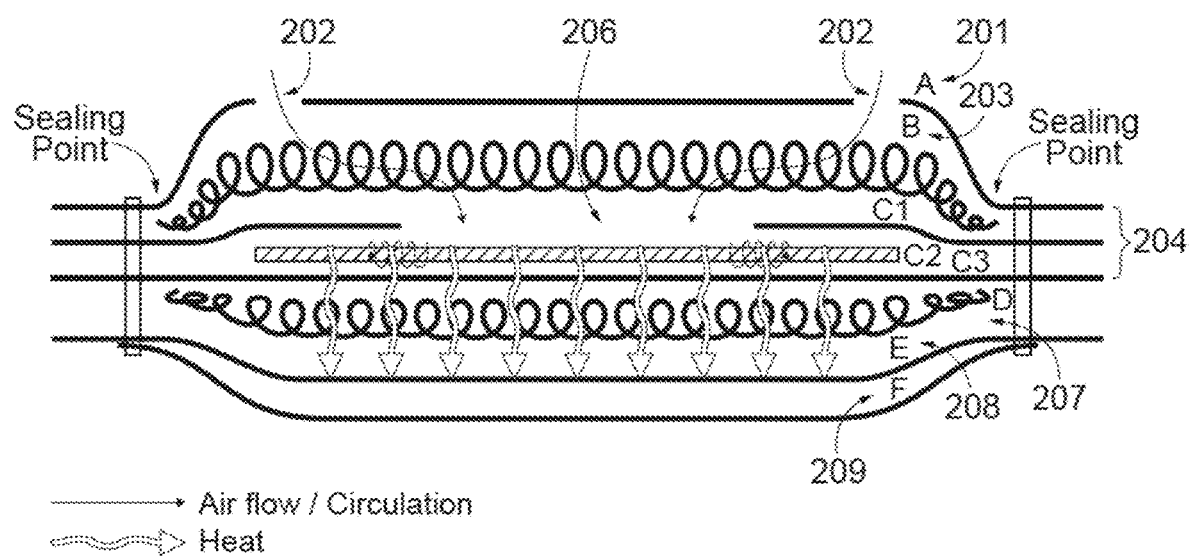
FIG. 4 shows a cross-sectional view of the cosmetic pad, depicting an exemplary schematic for the self-heating mechanism housed within the cosmetic pad, according to an embodiment.

FIG. 4 shows a cross-sectional view of the cosmetic pad 100, depicting an exemplary schematic for the self-heating mechanism housed within the cosmetic pad 100 upon activation of the heat source. In the embodiment shown, an air-activated heating element is used in the heating layer 204. As shown, air enters the cosmetic pad 100 via ventilating apertures 202 on the ventilating layer 201 through the air diffusing layer 203. In embodiments where the ventilating layer 201 is made of a breathable material, air would enter freely throughout the layer 201 without requiring apertures 202. Heating element 211 is activated when air enters the heating layer 204 via aperture 206, thereby heating the cosmetic pad 100 and the formulation comprising the cosmetic agent present in formulation chamber 207. Cosmetic pad 300 shown in FIG. 3 would function similarly with the self-heating element 304 being activated when the cosmetic pad 300 is removed from the sealed package 320.

Figure 5A:
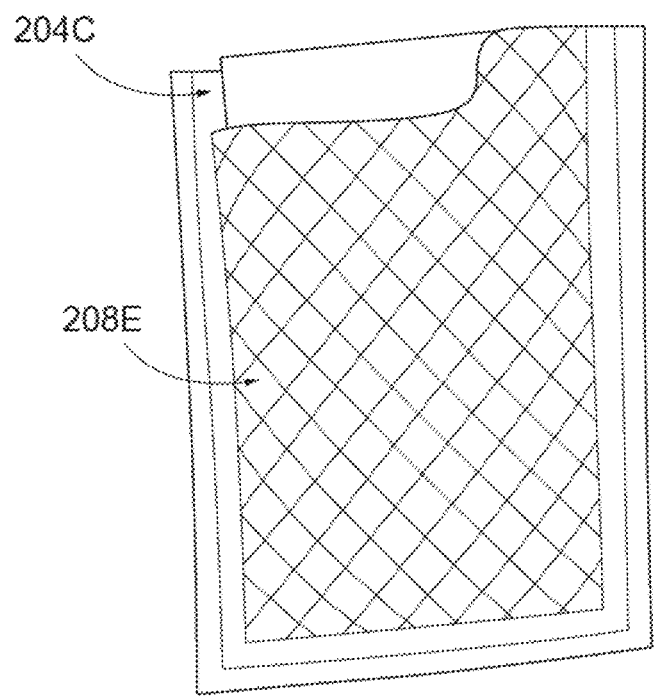
FIG. 5A shows the cosmetic pad with the heating layer exposed.
Figure 5B:
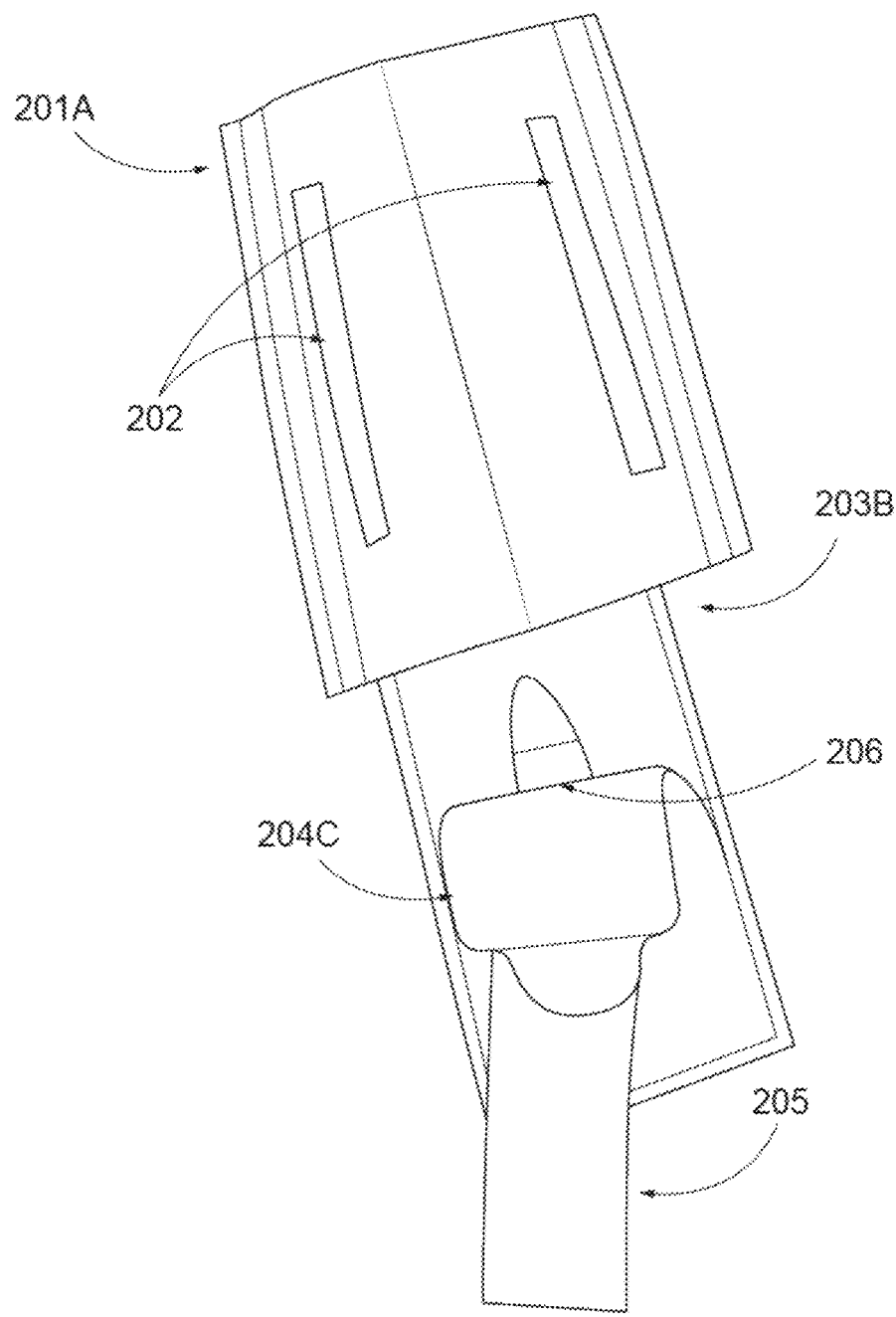
FIG. 5B shows an alternative exemplary self-heating cosmetic pad.

FIG. 5A shows the cosmetic pad 100 with the heating layer 204 exposed under skin contact layer 208.

FIG. 5B shows an alternative exemplary with a pull-tab mechanism 205 for activating the self-heating mechanism of the heating layer 204.

Figure 6:
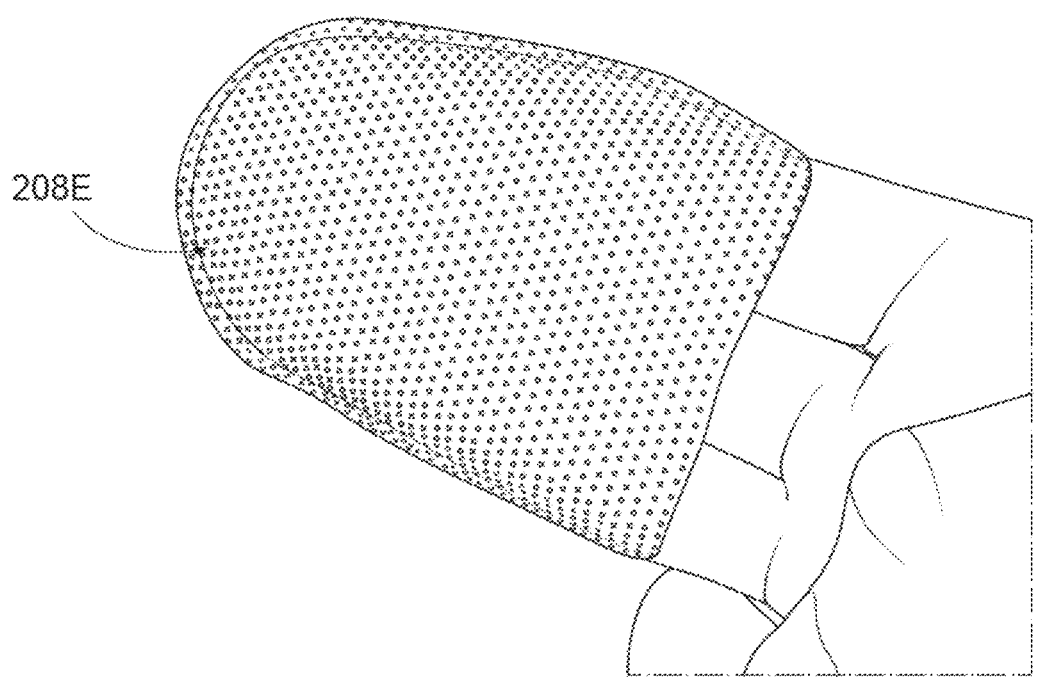
FIG. 6 shows the skin contact side of a cosmetic pad, according to an embodiment.

FIG. 6 shows the skin contact side of a cosmetic pad, according to an embodiment. As shown, if the cosmetic pad 100 or cosmetic pad 300 is to be used with the fingers for manual application, cleansing, skin lightening, brightening, smoothening, exfoliation, to name a few. The cosmetic pad may be provided with a pocket to accommodate one or more fingers.

The cosmetic pad 100 or 300 may be of any shape or sizes, including oval, elliptical, heart shaped, cone shaped, circular, square, rectangle, or any other possible shapes and be of any size including to eye, face, body or hair application, as appropriate for the desired function and use.

Another aspect of the present disclosure is directed to a hand treatment or a feet treatment system comprising the cosmetic pad described herein. The air activated self-heating technology in the cosmetic pad and the cosmetic agents provide a prolonged temperature control while enhancing the delivery of cosmetic agents. Such a treatment system for hands and/or feet constructed with a preloaded treatment formulation, comprising at least one self-contained and self-activated heating source enhances the efficacy of the treatment. The system described herein may be directed for a single-use and may be utilized on-the-go.

Figure 18:
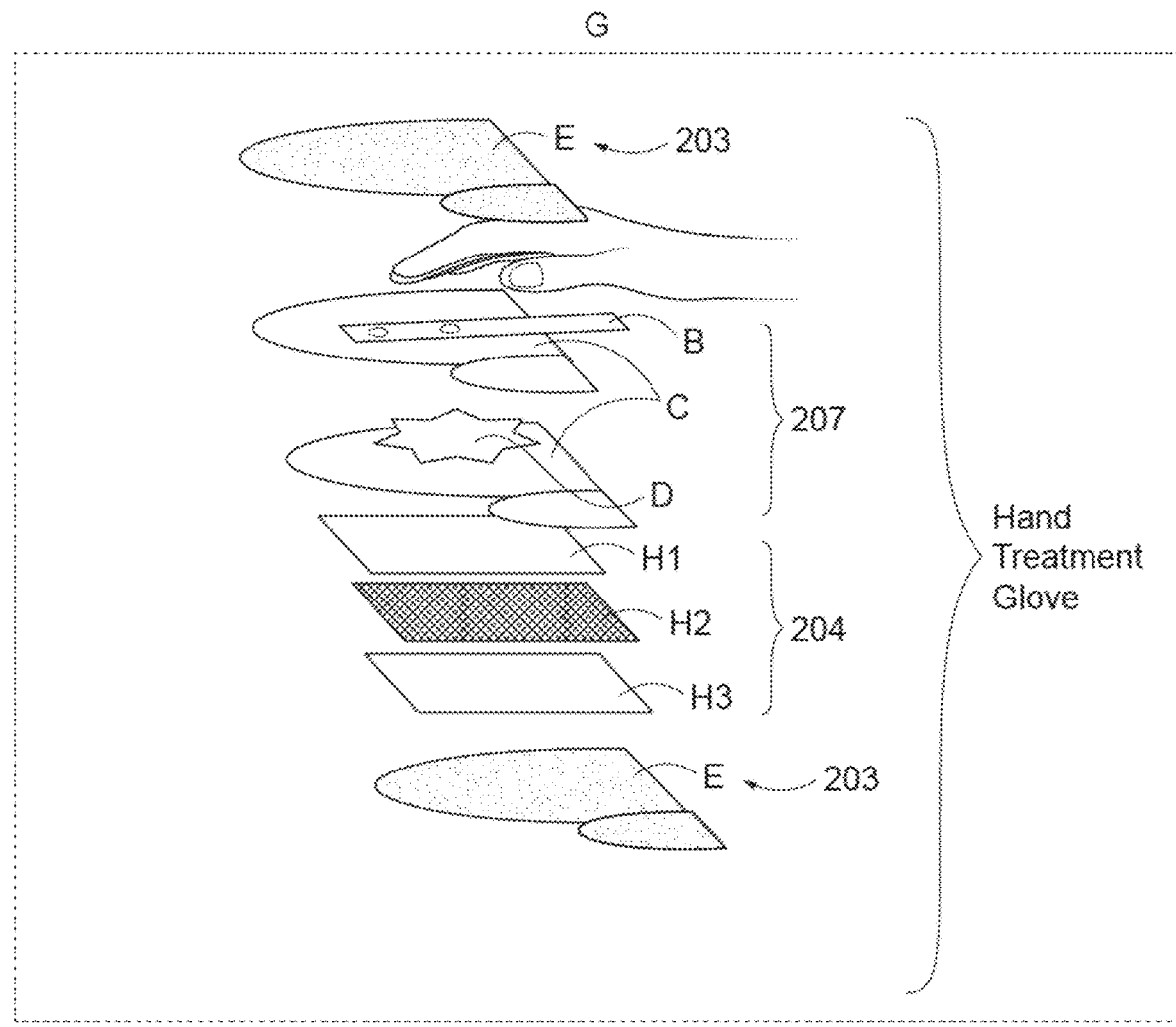
FIG. 18 shows an exemplary hand treatment system.

FIG. 18 shows the embodiment of a glove comprising the cosmetic pad. As shown in the figure, layer E is the air-diffusing layer, 203 and is present on the top and on the bottom of the glove. Layer F, i.e., the skin contact layer (208) and Layer A, i.e., the ventilating layer (202) are absent.

Figure 19:
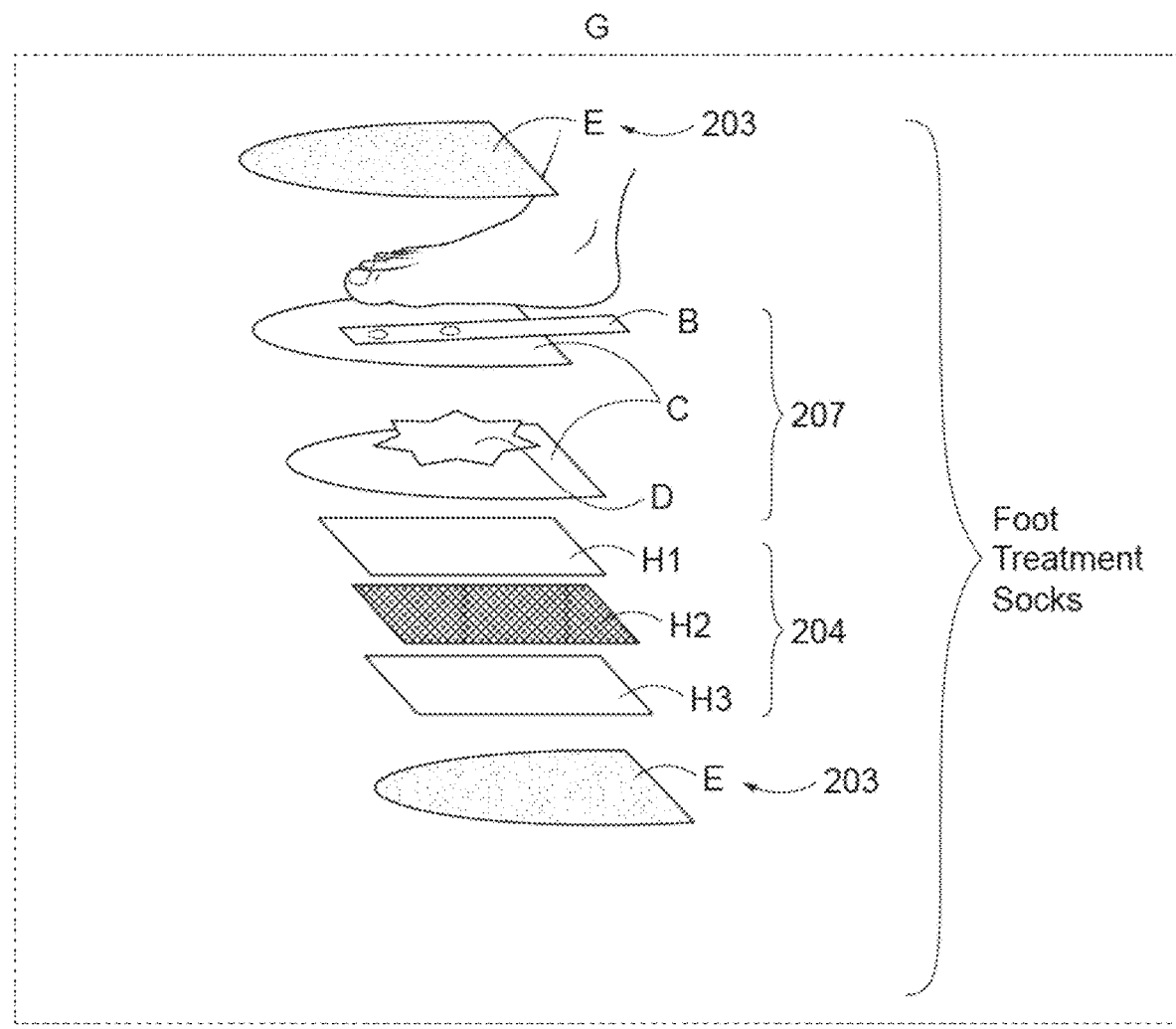
FIG. 19 shows an exemplary feet treatment system.

Similarly, FIG. 19 shows the embodiment of a sock comprising the cosmetic pad. As shown in the figure, layer E is the air-diffusing layer, 203 and is present on the top and on the bottom of the sock. Layer F, i.e., the skin contact layer (208) and Layer A, i.e., the ventilating layer (202) are absent.

Experiments

To demonstrate the difference in heating profile of the heating mechanism(s) between embodiments having an air-diffusing layer and embodiments without an air-diffusing layer, experiments were performed as described below.

Figure 7:
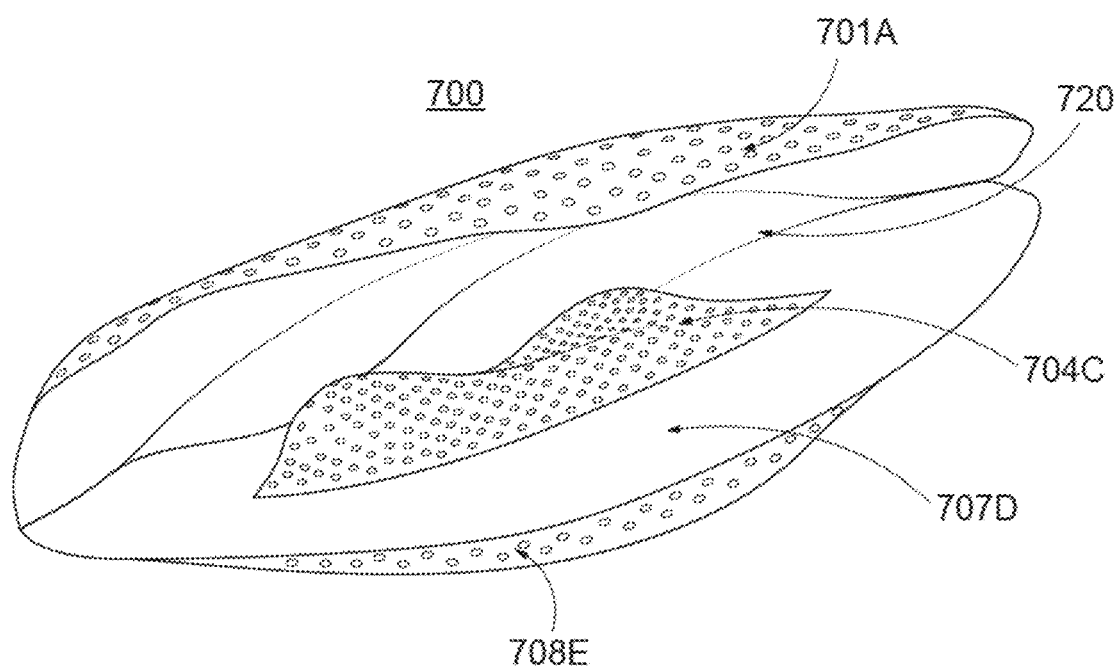
FIG. 7 shows a cross-sectional view of a cosmetic pad, without the air-diffusing layer, according to an embodiment.

FIG. 7 shows a cross-sectional view of a cosmetic pad 700, without the air-diffusing layer, according to an embodiment. The cosmetic pad 700 includes a ventilating layer 701 on one side (e.g., top side), as shown in this embodiment. The ventilating layer is constructed of a breathable material. The cosmetic pad 700 also includes a heating layer 704 similar to heating layer 204 shown in FIGS. 2A and 2B. The cosmetic pad 700 further includes a formulation layer 707, which may be a formulation chamber or pouch. The formulation layer houses the treatment product formulation which comprising the cosmetic agent. The cosmetic pad 700 also has a skin contact layer 708 on the bottom side. In the embodiment shown, finger pocket 720 is provided to allow one or more fingers to be inserted into the pocket 720 as shown in FIG. 6.

To carry out the experiment, the formulation layer 707 is filled with a formulation comprising a cosmetic agent and the heating element 704 is activated. Temperature readings were taken using a digital thermometer, such as the HH509 available from E Omega, coupled to an area of skin on a subject ("target area") by maintaining the temperature probe on the skin. Thermal images were also taken using a thermal camera, such as Thermal Camera FLIR A655sc Lens FOL25. The cosmetic pad 700 is placed on the target area of the subject with the skin contact layer 708 contacting the target area. The cosmetic pad 700 is allowed to heat up for an initial warming period of ninety (90) seconds. Then the cosmetic pad 700 is manually rubbed against the target area and the formulation is released onto the skin. An initial temperature reading is taken of the target area and recorded.

Figure 8A:
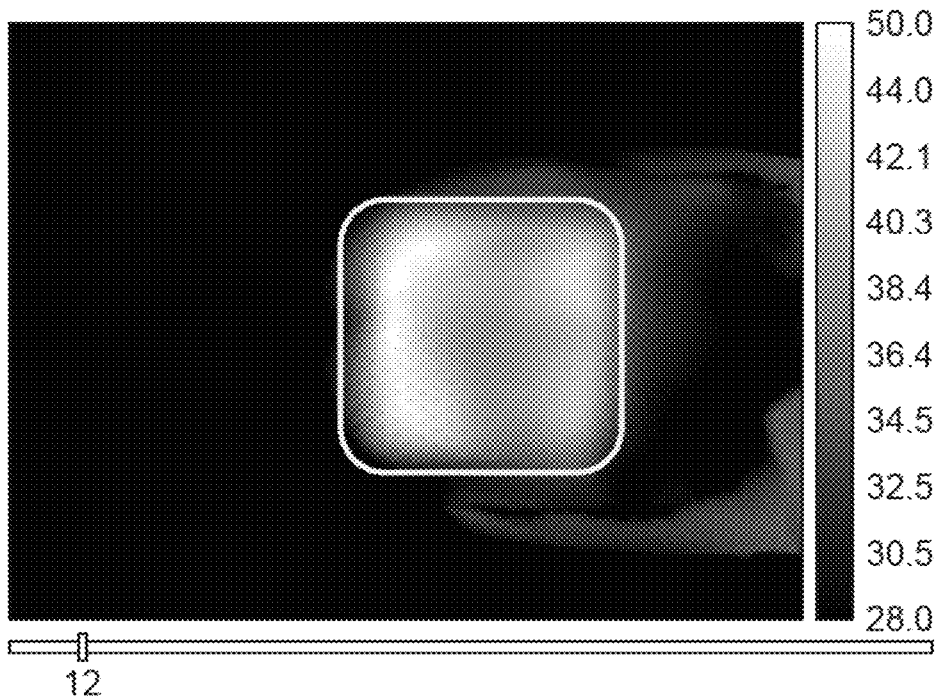
FIG. 8A shows a thermal image of the cosmetic pad of FIGS. 6 and 7 (applicator without air diffusing layer) after a ninety second initial warming followed by sixty second rubbing on skin, with finger(s) in a pad pocket.
Figure 8B:
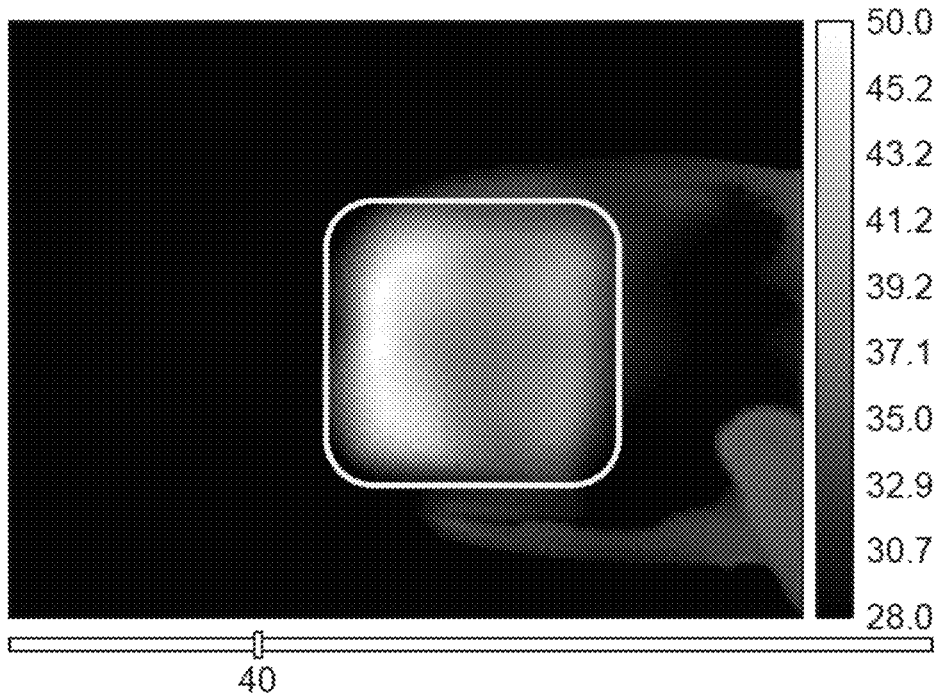
FIG. 8B shows a thermal image of the cosmetic applicator of FIG. 8A after an additional thirty seconds with finger still in the pad pocket.
Figure 8C:
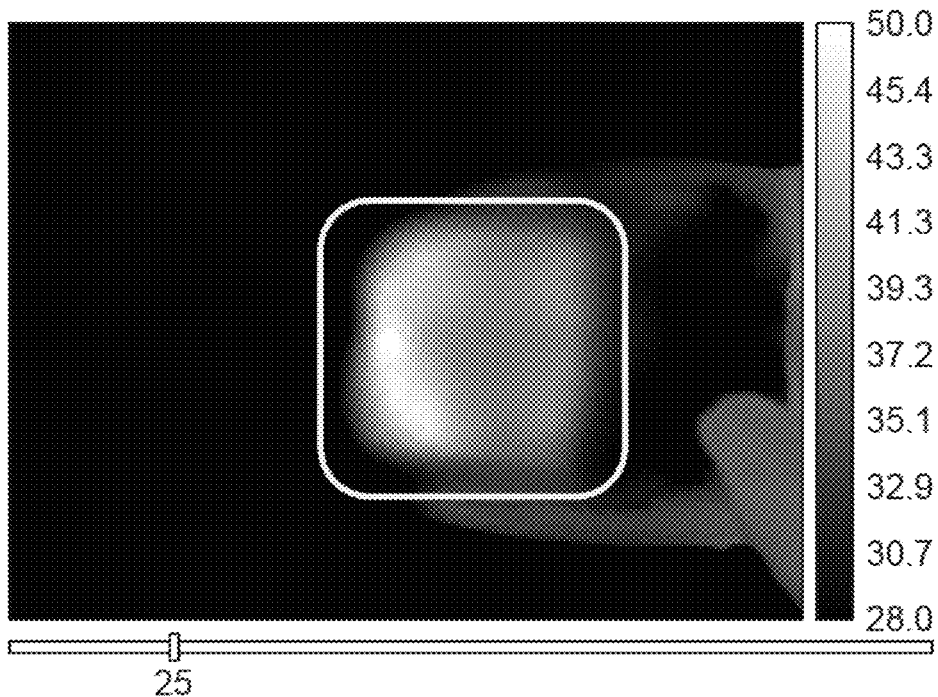
FIG. 8C shows a thermal image of the cosmetic applicator of FIG. 8B after an additional thirty seconds (sixty seconds after thermal image of FIG. 8A) with finger still in the pad pocket.
Figure 8D:
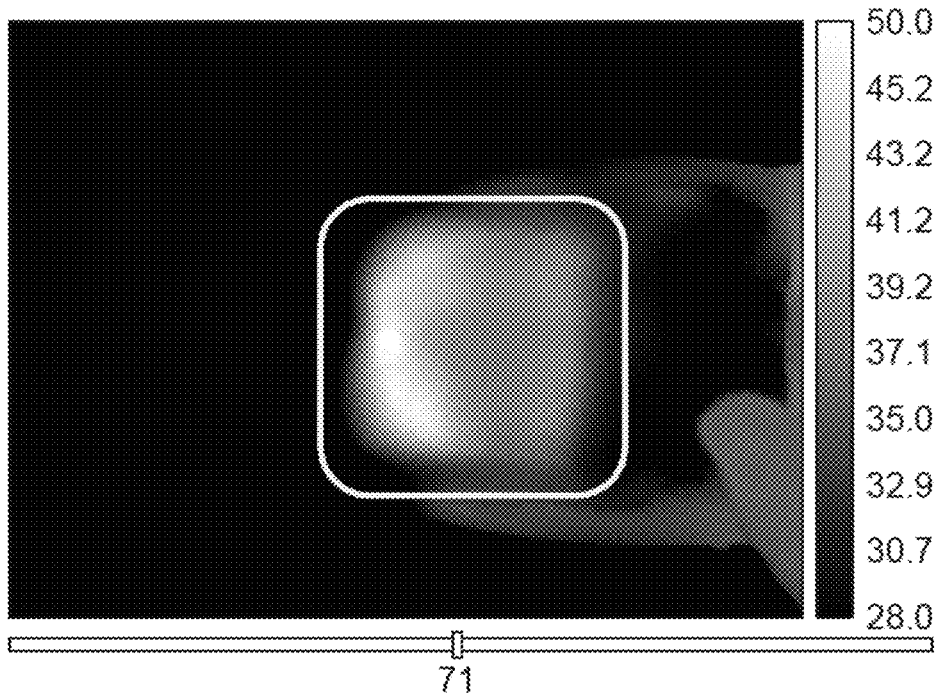
FIG. 8D shows a thermal image of the cosmetic applicator of FIG. 8C after an additional sixty seconds (two minutes after thermal image of FIG. 8A) with finger still in the pad pocket.
Figure 8E:
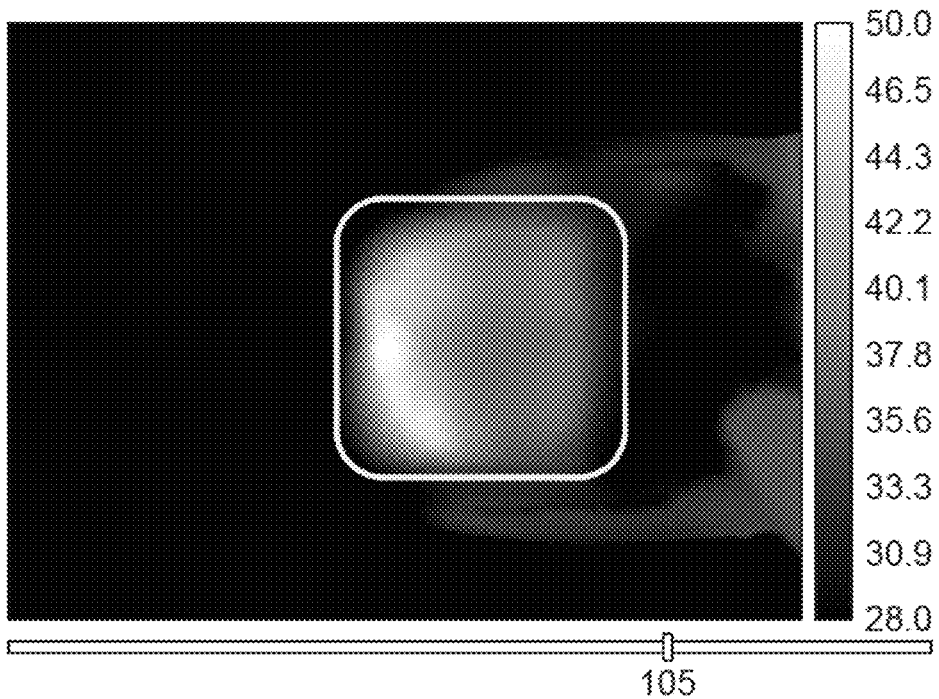
FIG. 8E shows a thermal image of the cosmetic applicator of FIG. 8D after an additional sixty seconds (three minutes after thermal image of FIG. 8A) with finger still in the pad pocket.

The thermal image is shown in FIG. 8A, with the hot spot (lighter/white areas) having a temperature of approximately 45° C., a cold spot (darker/grey area) temperature of approximately 37° C., and an average temperature (area within the white square) of approximately 41° C. Another reading is taken after rubbing the cosmetic pad on the skin for thirty (30) seconds. The thermal image of which is shown in FIG. 8B, showing the hot spot (lighter/white areas) having a temperature of approximately 46° C., a cold spot (darker/grey area) temperature of approximately 37° C., and an average temperature of approximately 40° C. Additional readings were taken at the one minute, two-minute, and three-minute marks after initial contact. As shown in FIG. 8C, one minute after temperature reading of FIG. 8A, the hot spot (lighter/white areas) has a temperature of approximately 47° C., a cold spot (darker/grey area) temperature of approximately 37° C., and an average temperature of approximately 40° C. As shown in FIG. 8D, two minutes after temperature reading of FIG. 8A, the hot spot (lighter/white areas) has a temperature of approximately 48° C., a cold spot (darker/grey area) temperature of approximately 37° C., and an average temperature of approximately 38° C. As shown in FIG. 8E, three minutes after temperature reading of FIG. 8A, the hot spot (lighter/white areas) has a temperature of approximately 48° C., a cold spot (darker/grey area) temperature of approximately 37° C., and an average temperature of approximately 39° C. The readings were taken with the fingers being kept in pocket 720.

As shown in FIGS. 8A-8E, the average temperature of the cosmetic pad 700 decreases over time and the size of the hot spot decreases over time, as the fingers in the pocket 720 hinder airflow to the heating element 704 without an air-diffusing layer.

Figure 9A:
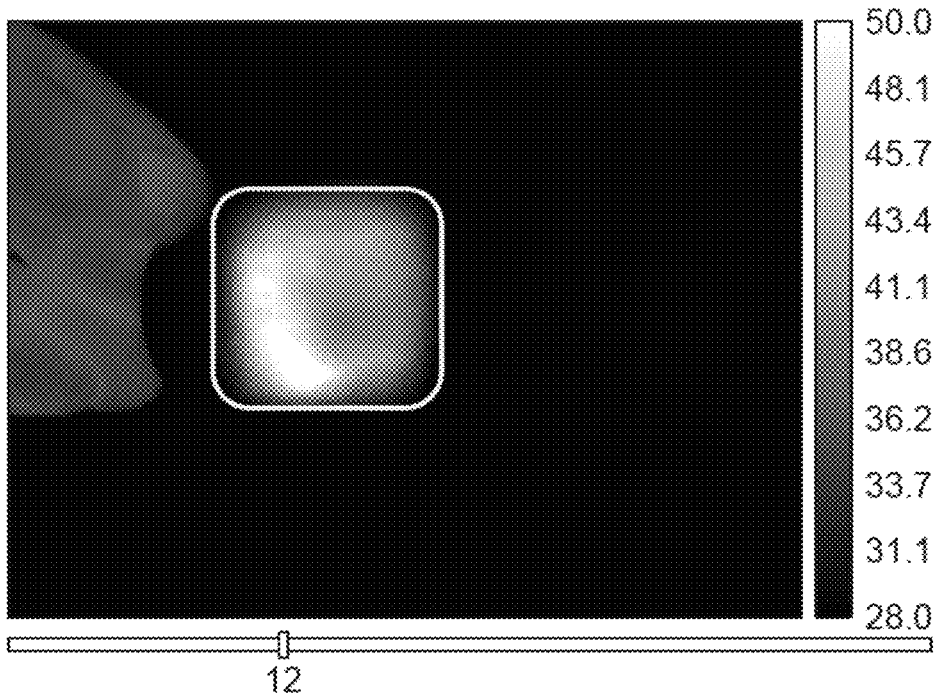
FIG. 9A shows a thermal image of the cosmetic applicator of FIG. 8E thirty seconds after removing the finger(s) from the pad pocket.
Figure 9B:
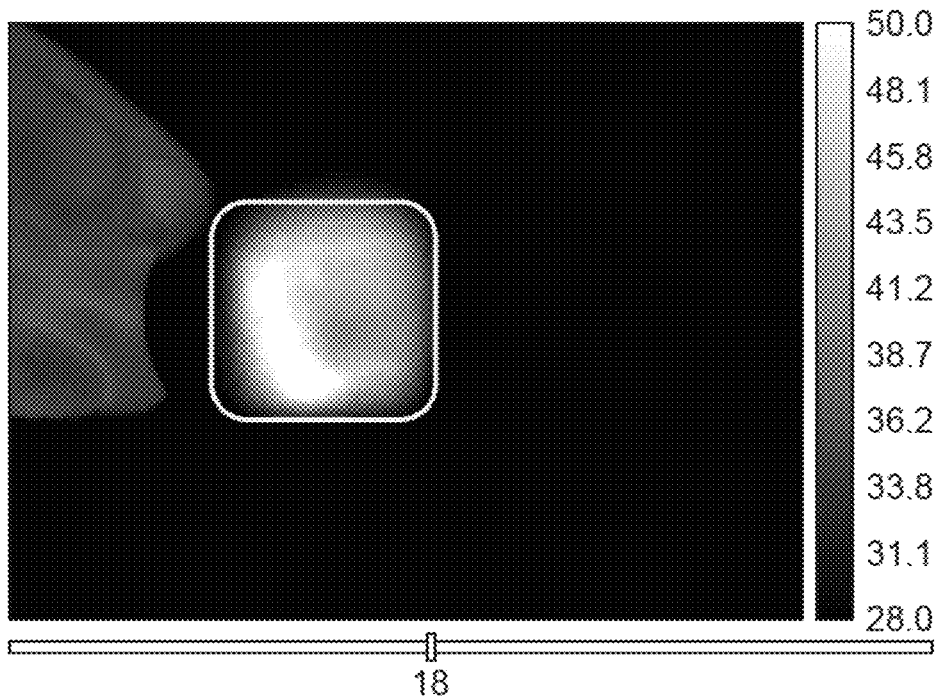
FIG. 9B shows a thermal image of the cosmetic applicator of FIG. 9A after an additional thirty seconds, totaling sixty seconds after removing the finger(s) from the pad pocket.
Figure 9C:
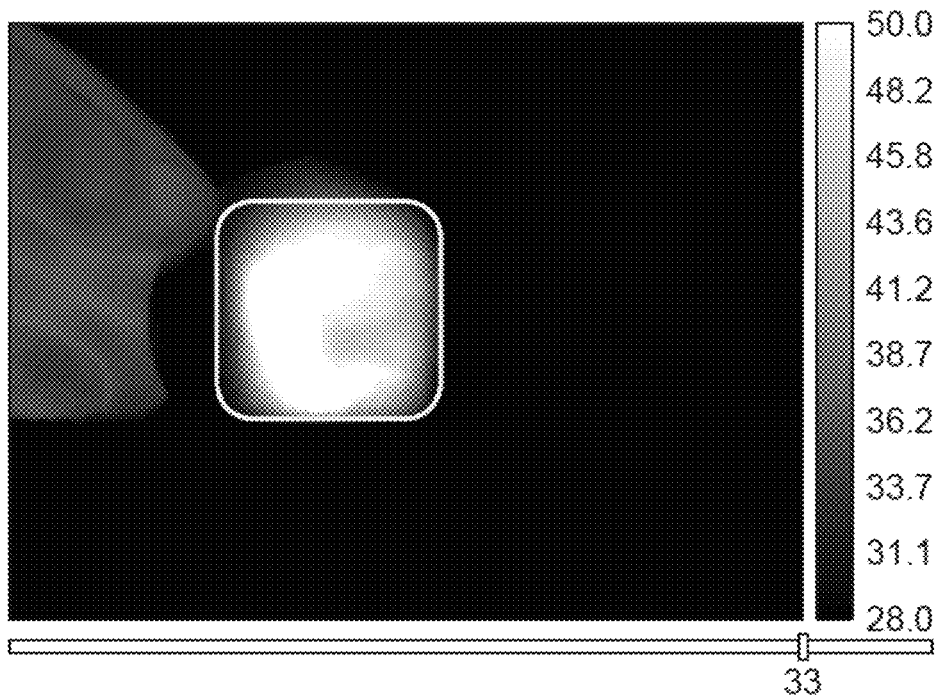
FIG. 9C shows a thermal image of the cosmetic applicator of FIG. 9B after an additional thirty seconds, totaling ninety seconds after removing the finger(s) from the pad pocket.

FIGS. 9A-9C show thermal images of the cosmetic pad 700 after the fingers were removed from pocket 720 following the thermal image shown in FIG. 8E. FIG. 9A shows a thermal image of the cosmetic pad 700 at 30 seconds after removing the fingers from the pocket 720. As shown, the hot spot (lighter/white areas) has a temperature of approximately 51° C., a cold spot (darker/grey area) temperature of approximately 39° C., and an average temperature (area inside the square) of approximately 43° C.

FIG. 9B shows a thermal image of the cosmetic pad 700 at the one-minute mark after removing the fingers from the pocket 720. The hot spot (lighter/white areas) has a temperature of approximately 54° C., a cold spot (darker/grey area) temperature of approximately 40° C., and an average temperature of approximately 46° C.

FIG. 9C shows a thermal image of the cosmetic pad 700 at ninety seconds after removing the fingers from the pocket 720. The hot spot (lighter/white areas) has a temperature of approximately 59° C., a cold spot (darker/grey area) temperature of approximately 43° C., and an average temperature of approximately 51° C.

As shown from FIGS. 9A-9C, the temperature of the cosmetic pad 700 increases over time and the hot spot area increases over time after the fingers were removed from the pocket 720, thereby allowing free flow of air to the heating element 704.

Figure 10:
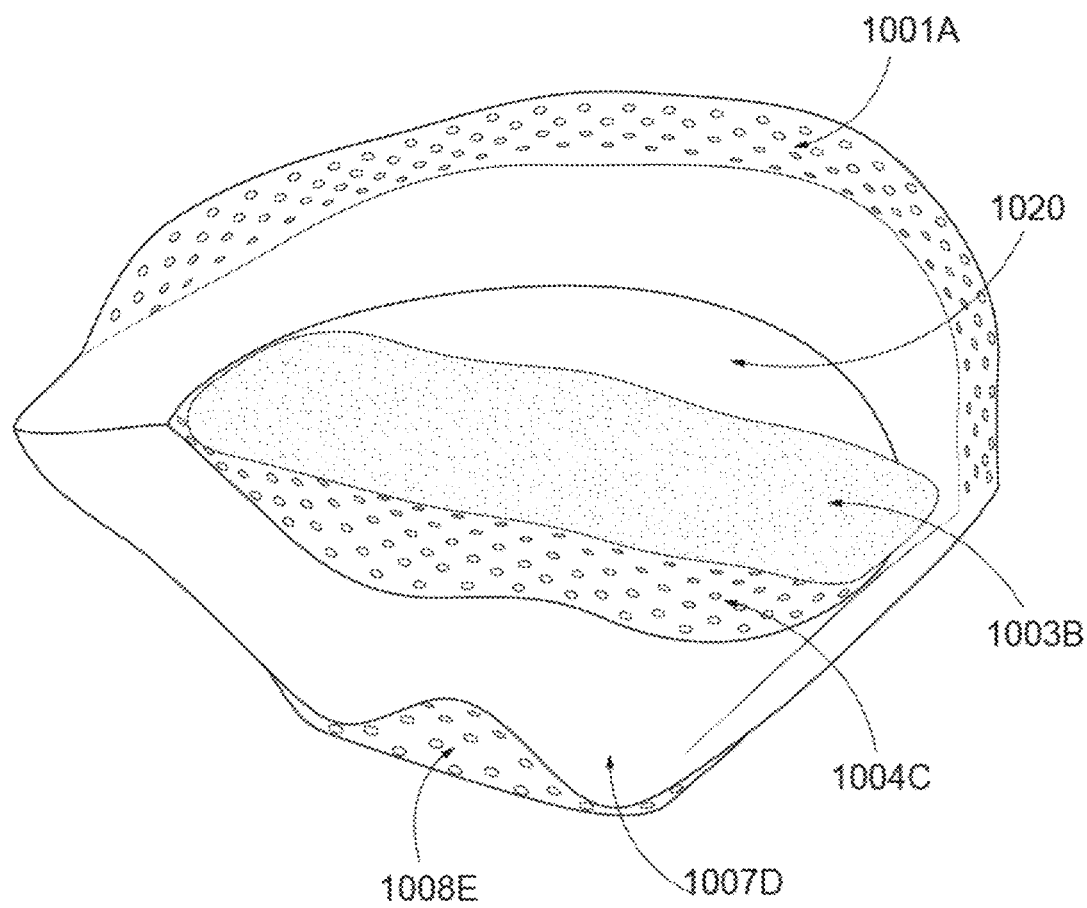
FIG. 10 shows a cross-sectional view of a cosmetic pad, with the air-diffusing layer, according to an embodiment.

FIG. 10 shows a cross-sectional view of a cosmetic pad 1000, with an air-diffusing layer 1003, according to an embodiment of the present disclosure. The air-diffusing layer 1003 as shown is constructed of PP, PET, or PE nonwovens. Similar to the experimental setup for the embodiment described above in FIG. 7, temperature readings were taken using a digital thermometer, such as the HH509 available from E Omega, coupled to a target area of skin on a subject by maintaining the temperature probe on the skin. Thermal images were also taken using a thermal camera, such as Thermal Camera FLIR A655sc Lens FOL25. The cosmetic pad 1000 includes formulation comprising cosmetic agent inside formulation layer 1004, and fingers may be placed inside the pocket 1020 for manual application of the cosmetic pad 1000. The cosmetic pad 1000 is placed on the target area on the subject with the skin contact layer 1008 contacting the target area. The cosmetic pad 1000 is allowed to heat up for an initial warming period of ninety (90) seconds. Then the cosmetic pad 1000 is manually rubbed against the target area and the formulation is released onto the skin. An initial temperature reading is taken of the target area and recorded.

Figure 11A:
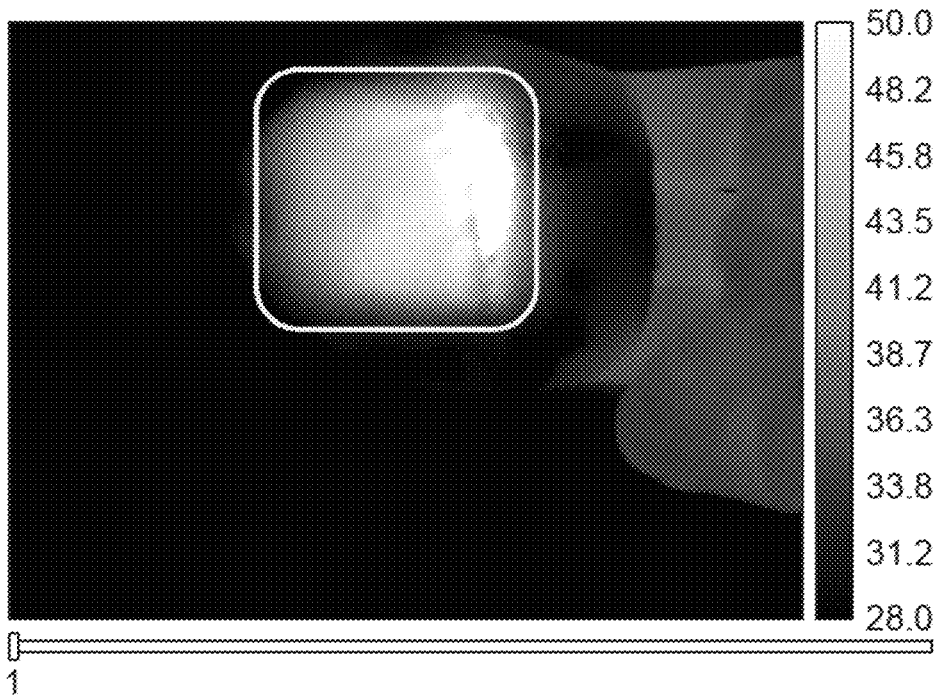
FIG. 11A shows a thermal image of the cosmetic pad of FIG. 11 (applicator with air diffusing layer) after a ninety second initial warming followed by sixty second rubbing on skin, with finger(s) in a pad pocket.
Figure 11B:
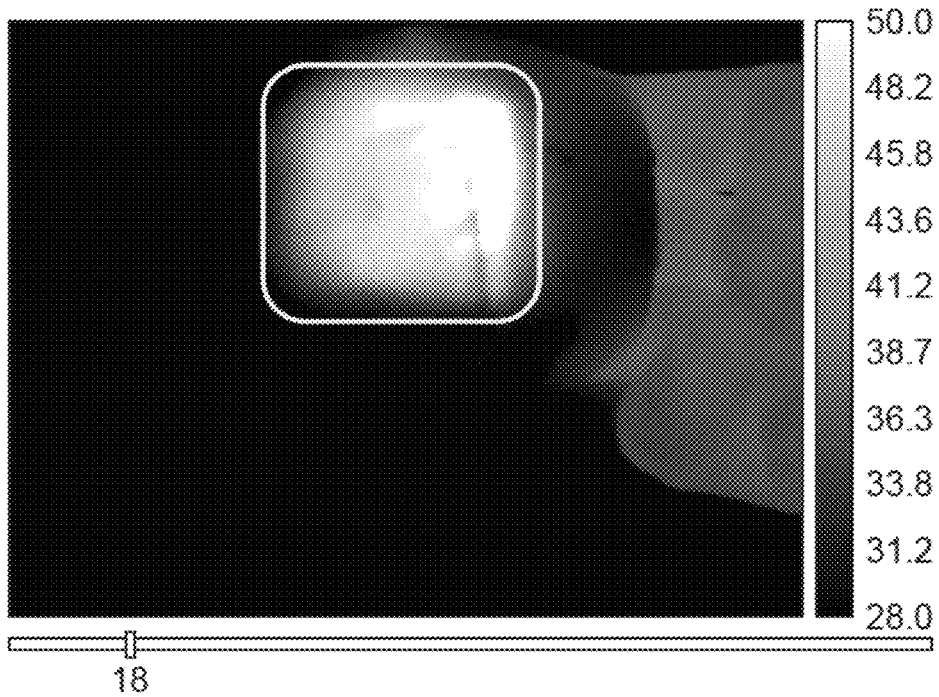
FIG. 11B shows a thermal image of the cosmetic pad of FIG. 12A after an additional thirty seconds with finger(s) still in the pad pocket.

The thermal image is shown in FIG. 11A, with the hot spot (lighter/white areas) having a temperature of approximately 48° C., a cold spot (darker/grey area) temperature of approximately 41° C., and an average temperature (area within the white square) of approximately 48° C. Another reading is taken after rubbing the cosmetic pad on the skin for thirty (30) seconds. The thermal image is shown in FIG. 11B, showing the hot spot (lighter/white areas) having a temperature of approximately 62° C., a cold spot (darker/grey area) temperature of approximately 47° C., and an average temperature of approximately 49.5° C. Additional readings were taken at the one minute, two-minute, and three-minute marks after initial contact.

Figure 11C:
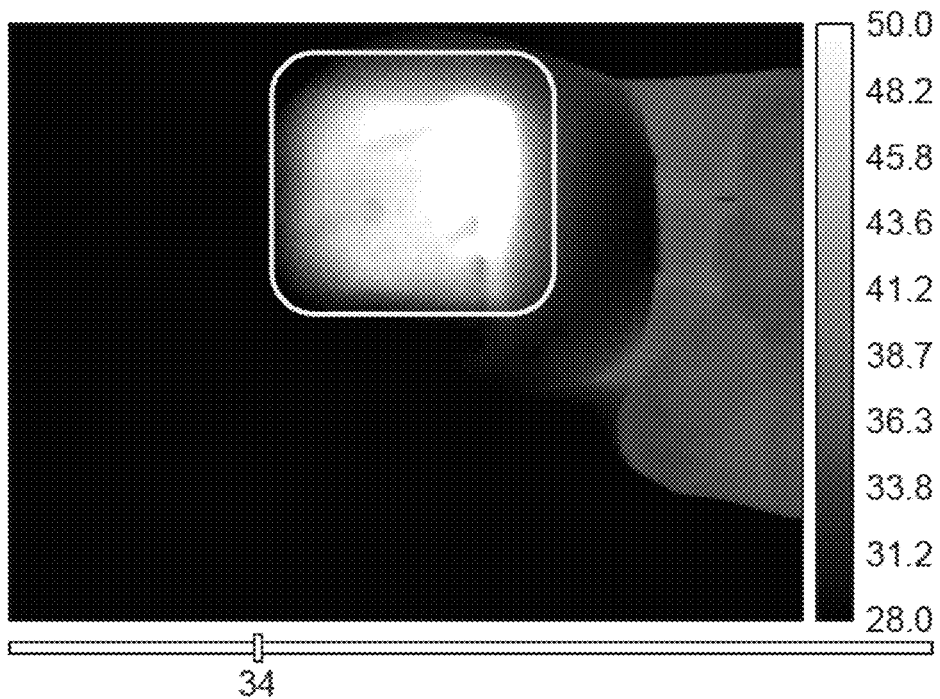
FIG. 11C shows a thermal image of the cosmetic pad of FIG. 12B after an additional thirty seconds (sixty seconds after thermal image of FIG. 12A) with finger still in the pad pocket.
Figure 11D:
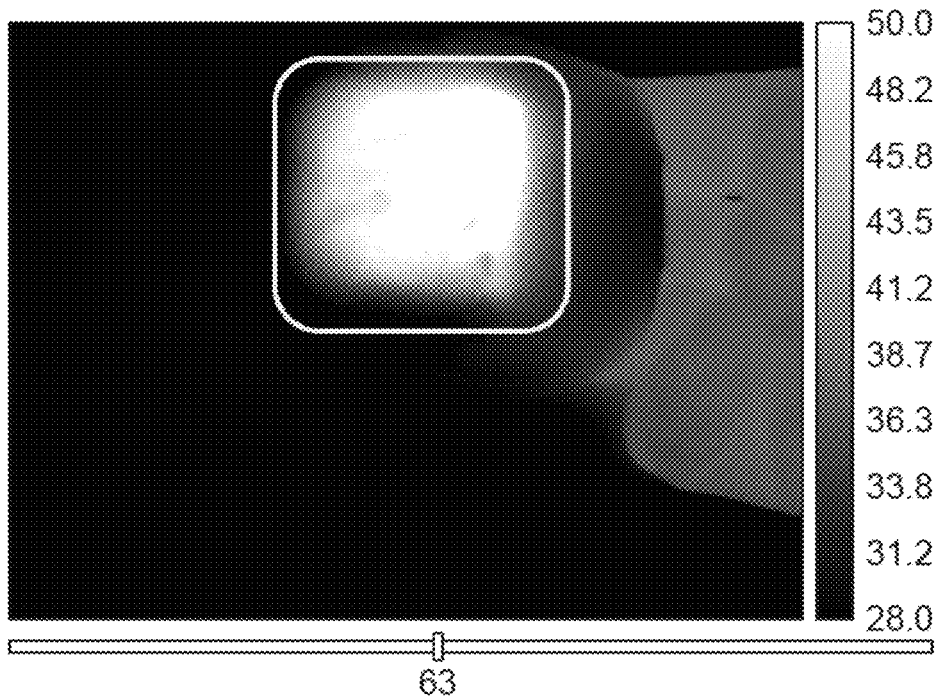
FIG. 11D shows a thermal image of the cosmetic pad of FIG. 12C after an additional sixty seconds (total two minutes after thermal image of FIG. 12A) with finger still in the pad pocket.
Figure 11E:
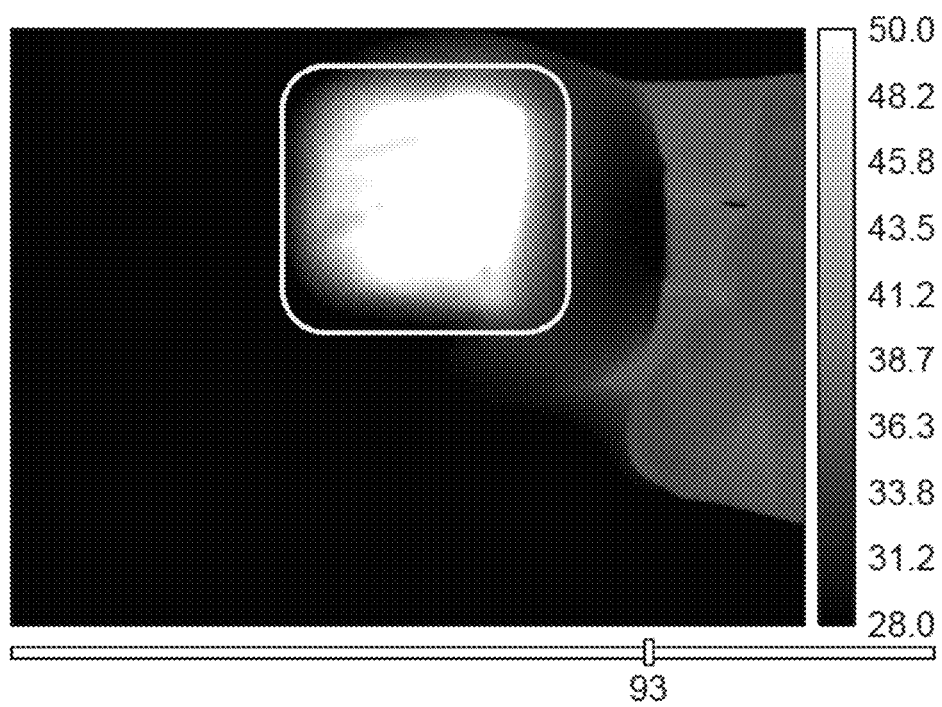
FIG. 11E shows a thermal image of the cosmetic pad of FIG. 12D after an additional sixty seconds (total three minutes after thermal image of FIG. 12A) with finger still in the pad pocket.

As shown in FIG. 11C, one minute after temperature reading of FIG. 11A, the hot spot (lighter/white areas) has a temperature of approximately 62° C., a cold spot (darker/grey area) temperature of approximately 47° C., and an average temperature of approximately 50° C. As shown in FIG. 11D, two minutes after temperature reading of FIG. 11A, the hot spot (lighter/white areas) has a temperature of approximately 64° C., a cold spot (darker/grey area) temperature of approximately 47° C., and an average temperature of approximately 53° C. As shown in FIG. 11E, three minutes after temperature reading of FIG. 11A, the hot spot (lighter/white areas) has a temperature of approximately 67° C., a cold spot (darker/grey area) temperature of approximately 48° C., and an average temperature of approximately 55° C. The readings were taken with the fingers being kept in pocket 1020. As shown in FIGS. 11A-11E, the average temperature of the cosmetic pad 1000 increases over time and the size of the hot spot increases over time, even with the fingers in the pocket 1020. As such, the air diffusing layer 1003 circulates and facilitates airflow within the cosmetic pad 1000, which provides the necessary spacing between fingers surface and heating element 1004. The spacing ensures proper air circulation for uninterrupted self-heating reaction function within the heater to generate continuous and constant heating during the application time, ranging from 30 seconds to 90 minutes.

Figure 12:
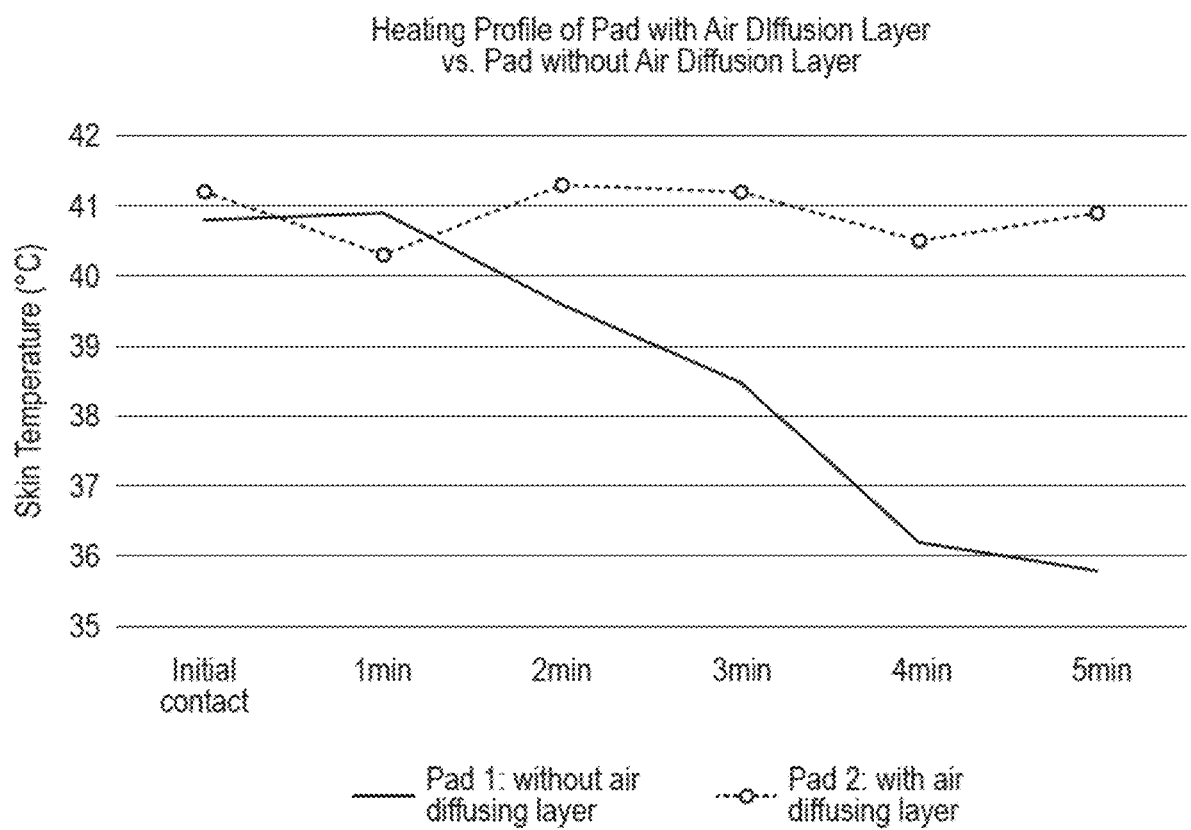
FIG. 12 shows a graph of heating profiles of a cosmetic pad with an air-diffusing layer and a cosmetic pad without an air-diffusing layer.

FIG. 12 shows a graph of temperature profiles for cosmetic pads with and without an air-diffusing layer. The temperature readings that make up the temperature profiles were measured with thermal coupling and are shown below in Table 1. The readings shown are actual skin temperature measurements obtained by taping a thermal couple (e.g., E OMEGA HH509 meter thermal couple temp probe) on a patch of skin on the back of a subject's hand. After initial activation of the heater by removing or breaking the seal of outer bag or outer layer, the heater was allowed to warm up for an initial heating period of approximately one minute. The cosmetic pad was then rubbed on the patch of skin where the thermal couple is secured (e.g., taped with a back and forth motion across). Temperature was then measured and recorded at one-minute intervals for five minutes. The solid black line represents temperature readings of the cosmetic pad without an air-diffusing layer, while the grey dotted line represents temperature readings of the cosmetic pad with an air-diffusing layer. As shown in the graph and in Table 1 below, the temperature of the cosmetic pads without an air-diffusing layer consistently decrease after one minute. The temperature of the cosmetic pad with an air-diffusing layer remained relatively consistent between initial reading after heat activation and five minutes after heat activation.

TABLE 1

Temperature Readings

| Cosmetic Pad | Air diffuser layer ("ADL") | skin temperature reading (° C.) | | | | | |
| --- | --- | --- | --- | --- | --- | --- | --- |
| | | Initial contact | 1 min | 2 min | 3 min | 4 min | 5 min |
| 1 | Without ADL | 40.8 | 40.9 | 39.6 | 38.5 | 36.2 | 35.8 |
| 2 | With ADL (3 layers of Fibertex nonwoven Tercie PP60 between finger pocket and heating layer) | 41.2 | 40.3 | 41.3 | 41.2 | 40.5 | 40.9 |

Figure 13:
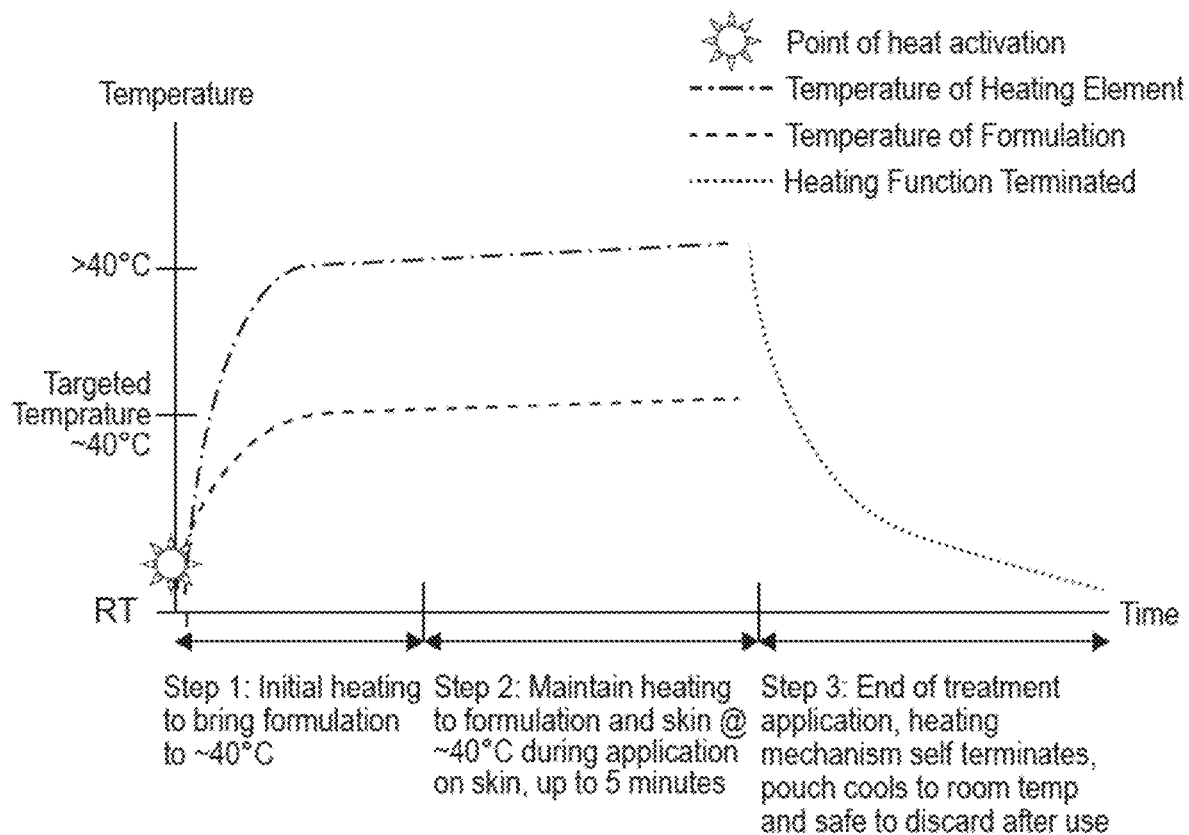
FIG. 13 shows a graph of a heating profile of a single stage heating cosmetic pad, according to an embodiment.

According to some embodiments, it may be desirous to have a cosmetic pad that heats up in a single stage, such as using a single heating source. FIG. 13 shows a graph of a heating profile of a single stage heating cosmetic pad, according to an embodiment. As shown in FIG. 13, a single stage heating pouch's heat delivery response and application Steps are as follows:

Step 1: Heating element reaches to a preset temperature when activated by removing sealed tab to expose air and initiating exothermic reaction. The heater heats up enclosed formulation's temperature to a desired temperature, e.g., approximately 40° C.;

Step 2: After the formula is heated to the desired temperature, the subject takes the warmed cosmetic pad, massages on skin for around 1-5 minutes to deliver the skin treatment; and Step 3: After treatment, the heating element's exothermic reaction stops, and the user may safely discard the cosmetic pad.

Single-stage heating requires approximately three to seven minutes or more to heat up the formulation to a temperature of 40° C. or more. Furthermore, a single-stage heating process delivers one temperature output throughout the entire usage period after initial activation.

Figure 14:
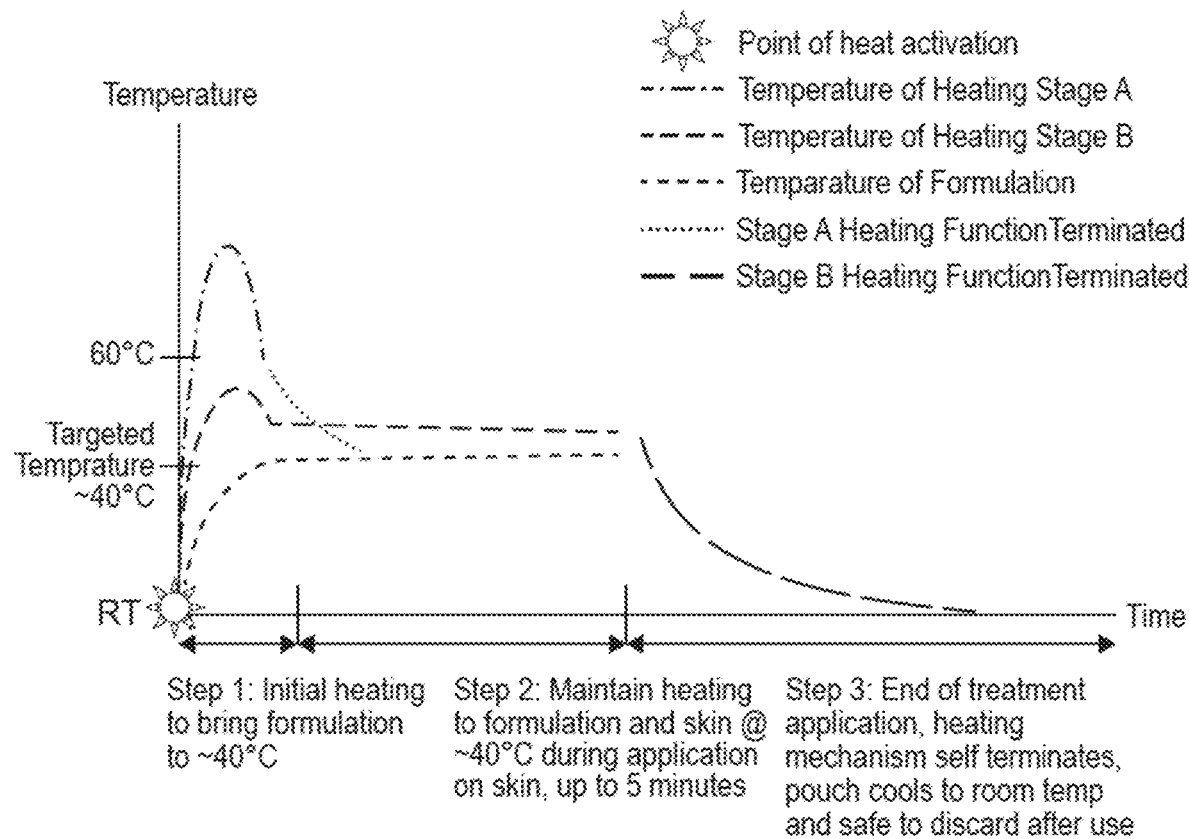
FIG. 14 shows a graph of a heating profile of a two-stage heating cosmetic pad, according to another embodiment.

In other embodiments, it may be desirous for the cosmetic pads to include more than one heating phase. FIG. 14 shows a graph of heating profiles of a dual-stage heating cosmetic pad, according to an embodiment of the present disclosure. A dual-stage heating mechanism changes the overall performance of the self-heating pads and the end subject's treatment product application experience. The heating element(s) deliver heat in two stages, each stage providing different heating outputs and timing intervals. An exemplary dual-stage heating process is described below with reference to FIG. 14:

Step 1: At Stage A, the formulation is warmed up with a short burst of intense heat to reach a targeted temperature, e.g., 40° C., faster than with a single stage heating process. This may reduce the initial waiting time for subject during Step 1, for example, by reducing the heating time to one minute;

Step 2: When stage A is completed, the Stage B heating will continue provide adequate heat to maintain the formulation's temperature while avoiding high/intense heat and causing discomfort on the skin/fingers during use;

Step 3: At the end of the treatment application, the heating elements self-terminate and the cosmetic pad cools to room temperature.

Advantageously, dual-stage heating provides a quicker initial warm up of the treatment product and the formulation to a desired temperature and potentially provides more control over the heating profile of the cosmetic pad by using multiple heating phases.

In alternative embodiments, the cosmetic pad may include multiple heating stages. For example, a third or fourth stage heating stage may be included to add bursts of heat during application.

Use/Application

According to an aspect of the present disclosure, a method of using the cosmetic pad, comprises following Steps:

Step 1: Opening the moisture bag G, which activates the heating element present in the cosmetic pad;

Step 2: Waiting for about 30 seconds to about 5 minutes, preferably about 1 minute to 1 minute 30 seconds;

Step 3: Sliding at least one finger to skin contact side (201 or 301) of the cosmetic pad;

Step 4: Pulling tab B as shown in FIG. 2A to release the formulation;

Step 5: Rubbing or applying the cosmetic pad, layer 208 (or 308) on the skin, including body, face, forearm, body, eyes or area around eyes, hair etc. for from about 30 seconds to about 30 minutes to release the formulation. According to an embodiment, the cosmetic pad may be used on the skin from about 2 minutes to about 10 minutes.

In various embodiments, the cosmetic pads may be provided for use with an applicator. Using an applicator is be desirable to avoid applying/using the cosmetic pads with fingers, e.g., for sanitary or safety purposes. For example, the cosmetic pad may include a strap on one side for inserting and securing one or more fingers during use. Many different applicators or devices are known in the art and all such applicators are encompassed within the disclosure of the present disclosure.

Figure 15A:
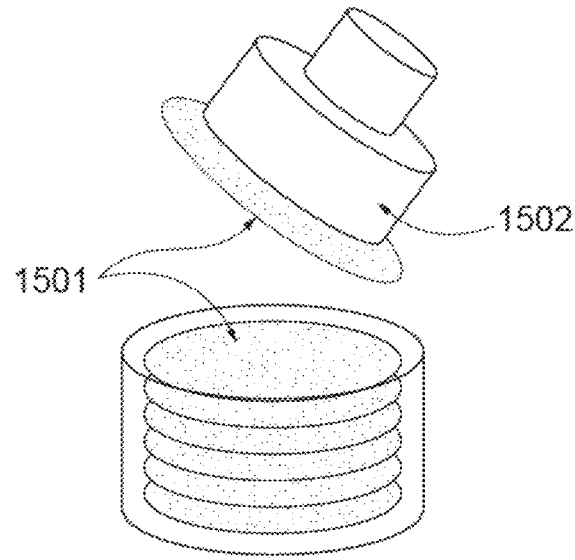
FIG. 15A shows an exemplary applicator for picking up the cosmetic pads, according to an embodiment.

FIG. 15A shows an exemplary applicator for picking up the cosmetic pads, according to an embodiment of the present disclosure. The applicator 1502 may be used to pick up cosmetic pad 1501 as shown, for example, via an adhesive mechanism, or a hook-and-loop fastening mechanism such as those commercially available from Velcro®.

Figure 15B:
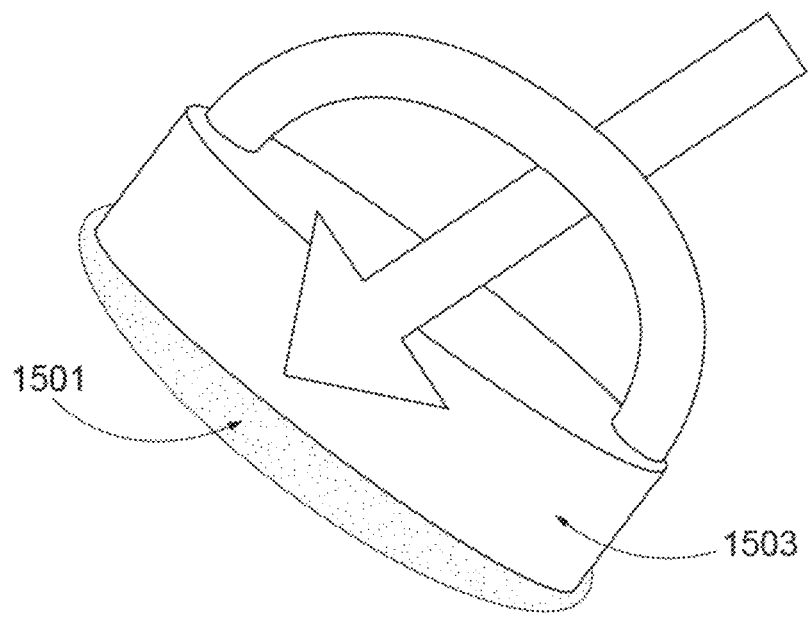
FIG. 15B shows another exemplary embodiment of an applicator for use with the cosmetic pads.

FIG. 15B shows another exemplary embodiment of an applicator for use with the cosmetic pads. The applicator 1503 may be used to pick up a cosmetic pad 1501 as shown. Suitable mechanisms for attaching the cosmetic pad 1501 to the applicator 1503 include, without limiting, weak adhesives, hook-and-loop fasteners, etc.

Figure 16:
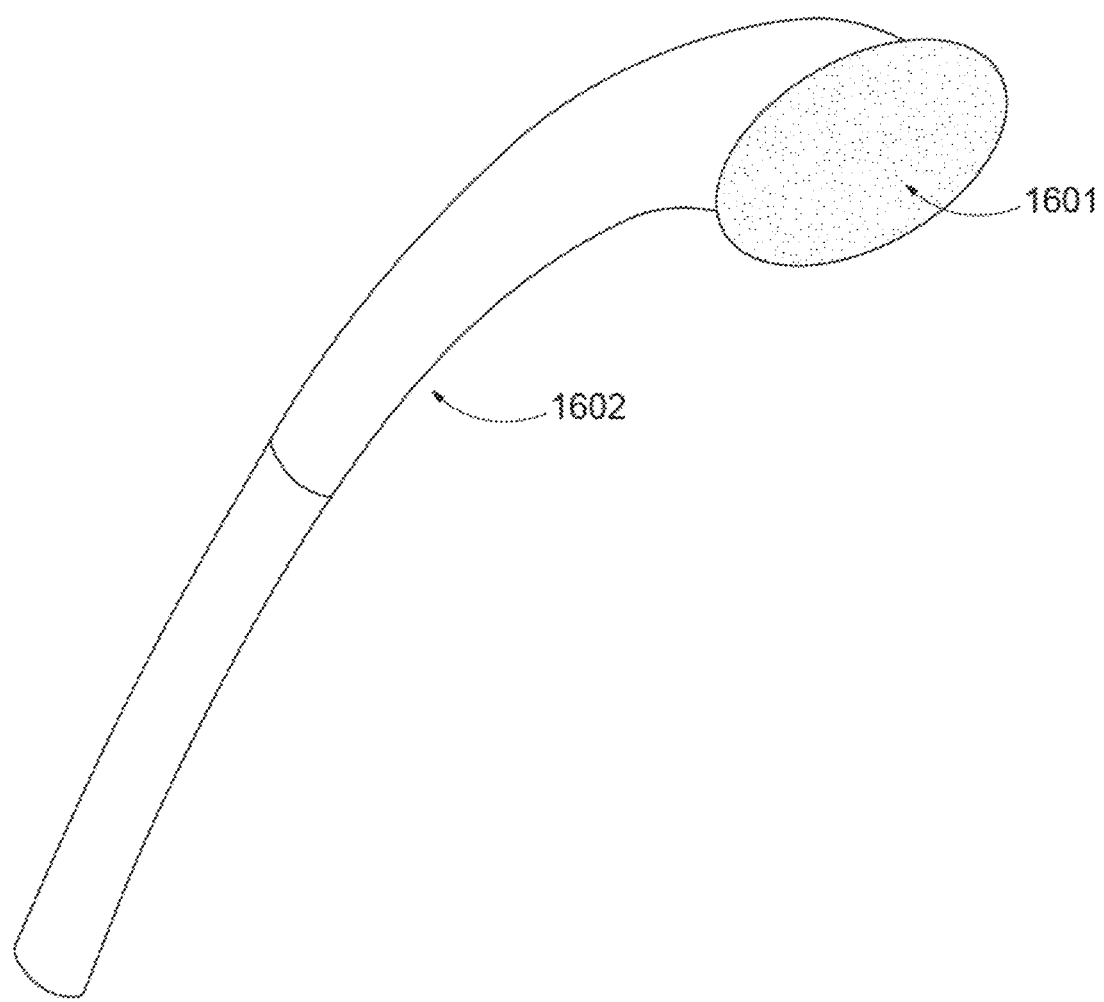
FIG. 16 shows an exemplary wand applicator for use with the cosmetic pads.
Figure 17:
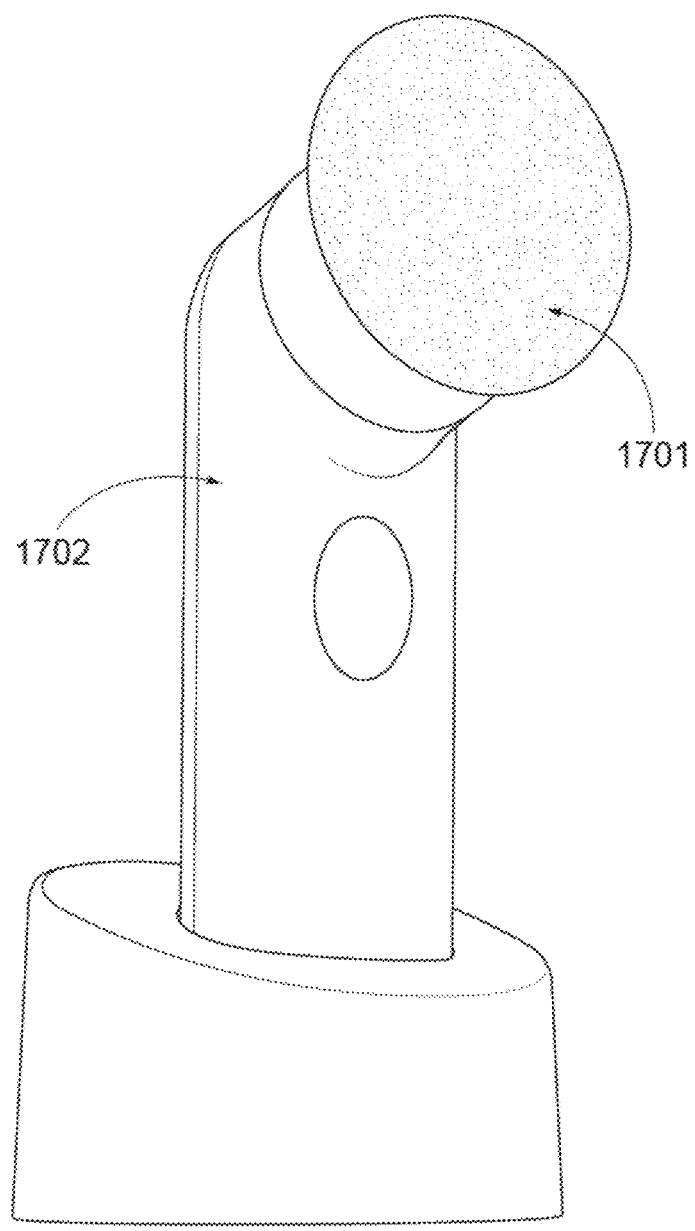
FIG. 17 shows an exemplary cleansing device for use with the cosmetic pads.

FIG. 16 shows an exemplary wand applicator for use with the cosmetic pads. The applicator 1602 may be used to pick up a cosmetic pad 1601 as shown. FIG. 17 shows an exemplary cleansing device 1702 for use with the cosmetic pads 1701. The cosmetic pads 1701 attaches to cleansing device 1702 via weak adhesive mechanisms, hook-and-loop fasteners, etc.

In embodiments where the cosmetic pads are used with applicators or devices, the ventilating layer may be configured in a manner to allow for free flow of air, e.g., ventilating apertures on the cosmetic pad would not be obstructed by the device or applicator. For example, the applicator may be configured with apertures corresponding to those on the cosmetic pads or configured with ventilating designs throughout the applicator to allow free flow of air through the cosmetic pad's ventilating layer.

Formulation

According to embodiments of the present disclosure, the treatment products contemplates any formulation of cosmetic agents, including peptides, small molecules, vitamins, cleansing agents, exfoliating agents, bio-actives, organic acid, individually or in mixtures, in unencapsulated or encapsulated forms and dermatologic agents. The number of treatment product(s) may be co-formulated.

In some embodiments, the cosmetic agent present in the formulation may cleanse, exfoliate, smooth or repair the skin, body or hair of the subject. In one embodiment, one treatment product may be present in the formulation housing. Yet in other embodiments, more than one treatment product may be housed in multiple and respective housings, each having different cosmetic or dermatologic benefit and purpose and each product may be activated and heated at a different rate with a varied release timing. All such combinations and permutations of the cosmetic agents are encompassed within the disclosure of the present disclosure.

According to an aspect of the present disclosure, the formulation comprising the cosmetic agent may be applied to mammalian keratinous tissue, to human skin, face or hair. The formulation comprising the cosmetic agents may be of various forms. For example, some non-limiting examples of such forms include solutions, suspensions, lotions, creams, gels, emulsions, suspension, toners, ointments, cleansing agents, exfoliating agents, liquid shampoos and hair conditioners, pastes, foams, powders, mousses, shaving creams, hydrogels, film-forming products, facial and skin masks, and the like.

In some embodiments, the cosmetic agent present in a formulation is unencapsulated. In some other embodiments, the cosmetic agent present in a formulation is encapsulated. Further, in specific embodiments, the cosmetic agent may be present in layer 708 or the cosmetic agent may be impregnated within layer 707, the top or bottom layer, such as, for example, between the pores of the layers.

According to one embodiment of the present disclosure, the formulation comprising the cosmetic or dermatologic agent includes peptides, small molecules, large molecules, proteins, vitamins, cleansing agents, exfoliating agents, bioactives, organic acid, including hyaluronic acid, tannic acid, oil, shampoo, conditioner, hair care agents, plant or fruit extracts, naturally occurring agents individually or in mixtures or combinations, in unencapsulated or encapsulated forms.

Nonlimiting examples of these additional cosmetic agents or ingredients include skin care actives such as peptides (e.g., Matrixyl (pentapeptide) derivative), farnesol, bisabolol, phytantriol, glycerol, urea, guanidine (e.g., amino guanidine); vitamins and derivatives thereof, such as ascorbic acid, vitamin A (e.g., retinoid derivatives such as retinyl palmitate or retinyl proprionate), vitamin E (e.g., tocopherol acetate), vitamin B.sub.3 (e.g., niacinamide) and vitamin B.sub.5 (e.g., panthenol) and the like and mixtures thereof; sunscreens; anti-acne medicaments (such as without limiting, resorcinol, salicylic acid, and the like; antioxidants (e.g., phytosterols, lipoic acid); flavonoids (e.g., isoflavones, phytoestrogens); skin soothing and healing agents such as, without limiting, aloe vera extract, allantoin and the like; chelators and sequestrants; and agents suitable for aesthetic purposes such as, essential oils, fragrances, skin sensates, opacifiers, aromatic compounds (e.g., clove oil, menthol, camphor, *eucalyptus* oil, and eugenol).

Nonlimiting examples of suitable carboxylic copolymers, emulsifiers, emollients, and other additional ingredients are disclosed in U.S. Pat. No. 5,011,681, to Ciotti et al., issued Apr. 30, 1991 and U.S. Pat. No. 5,939,082, to Oblong et al., issued Aug. 17, 1999, both of which are herein incorporated by reference. The above described vitamin B.sub.3 compounds may be incorporated as re-crystallized crystals that remain in crystalized form in the cosmetic agent or as partially solubilize crystals (i.e., some of the crystals are dissolved and some remain in crystalline form in the cosmetic agent).

In an embodiment, where the cosmetic agent is to be in contact with human keratinous tissue, i.e., skin, face or hair, the additional components should be suitable for application to keratinous tissue. That is, when incorporated into the cosmetic agent(s), they are suitable for use in contact with human keratinous tissue without undue toxicity, incompatibility, instability, allergic response, and is within the scope of sound scientific judgment.

The CTFA Cosmetic Ingredient Handbook, Second Edition (1992) describes a wide variety of nonlimiting cosmetic and pharmaceutical ingredients commonly used in the skin care industry, which are suitable for use in the cosmetic agents of the present disclosure. Examples of these ingredient classes include abrasives, absorbents, aesthetic components such as fragrances, pigments, colorings/colorants, essential oils, skin sensates, astringents, etc. (e.g., clove oil, menthol, camphor, *eucalyptus* oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the cosmetic agent (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins and derivatives thereof.

The topical cosmetic agents of the present disclosure may contain a safe and effective amount of farnesol. Farnesol is a naturally occurring substance which is believed to act as a precursor and/or intermediate in the biosynthesis of squalene and sterols, especially cholesterol. Farnesol is also involved in protein modification and regulation (e.g., farnesylation of proteins), and there is a cell nuclear receptor which is responsive to farnesol.

Chemically, farnesol is [2E,6E]-3,7,11-trimethyl-2,6,10-dodecatrien-1-ol and as used herein "farnesol" includes isomers and tautomers of such. Farnesol is commercially available, e.g., under the names farnesol (a mixture of isomers from Dragoco, 10 Gordon Drive, Totowa, N.J.) and trans-trans-farnesol (Sigma Chemical Company, P.O. Box 14508, St. Louis, Mo.).

When present in the cosmetic agents of the present disclosure, the cosmetic agent preferably contains from about 0.001% to about 50%, by weight of the cosmetic agent, more preferably from about 0.01% to about 20%, even more preferably from about 0.1% to about 15%, even more preferably from about 0.1% to about 10%, still more preferably from about 0.5% to about 5%, and still more preferably from about 1% to about 5% by weight of the cosmetic agent.

The topical cosmetic agents of the present disclosure may contain a safe and effective amount of phytantriol. Phytantriol is the common name for the chemical known as 3,7,11,15, tetramethylhexademaye-1,2,3,-triol. Phytantriol is commercially available from BASF (1609 Biddle Avenue, Whyandotte, Mich.). For example, phytantriol is useful as a spider vessel/red blotchiness repair agent, a dark circle/puffy eye repair agent, sallowness repair agent, a sagging repair agent, an anti-itch agent, a skin thickening agent, a pore reduction agent, oil/shine reduction agent, a post-inflammatory hyperpigmentation repair agent, wound treating agent, an anti-cellulite agent, and regulating skin texture, including wrinkles and fine lines.

In the cosmetic agents of the present disclosure, the phytantriol preferably is included in an amount from about 0.001% to about 50% by weight of the cosmetic agent, more preferably from about 0.01% to about 20%, even more preferably from about 0.1% to about 15%, even more preferably from about 0.2% to about 10%, still more preferably from about 0.5% to about 10%, and still more preferably from about 1% to about 5%.

A safe and effective amount of a desquamation active may be added to the cosmetic agents of the present disclosure, more preferably from about 0.1% to about 10%, even more preferably from about 0.2% to about 5%, also preferably from about 0.5% to about 4%, by weight of the cosmetic agent. Desquamation actives enhance the skin appearance benefits of the present disclosure. For example, the desquamation actives tend to improve the texture of the skin (e.g., smoothness). One desquamation system that is suitable for use herein contains sulfhydryl compounds and zwitterionic surfactants and is described in U.S. Pat. No. 5,681,852, to Bissett, incorporated herein by reference. Another desquamation system that is suitable for use herein contains salicylic acid and zwitterionic surfactants and is described in U.S. Pat. No. 5,652,228 to Bissett, incorporated herein by reference. Zwitterionic surfactants such as described in these applications are also useful as desquamatory agents herein, with cetyl betaine being particularly preferred.

The cosmetic agents of the present disclosure may contain a safe and effective amount of one or more anti-acne actives. Examples of useful anti-acne actives include resorcinol, sulfur, salicylic acid, benzoyl peroxide, erythromycin, zinc, etc. Further examples of suitable anti-acne actives are described in further detail in U.S. Pat. No. 5,607,980, issued to McAtee et al, on Mar. 4, 1997.

The cosmetic agents of the present disclosure may further contain a safe and effective amount of one or more anti-wrinkle actives or anti-atrophy actives. Exemplary anti-wrinkle/anti-atrophy actives suitable for use in the cosmetic agents of the present disclosure include sulfur-containing D and L amino acids and their derivatives and salts, particularly the N-acetyl derivatives, a preferred example of which is N-acetyl-L-cysteine; thiols, e.g., ethane thiol; hydroxy acids (e.g., alpha-hydroxy acids such as lactic acid and glycolic acid or beta-hydroxy acids such as salicylic acid and salicylic acid derivatives such as the octanoyl derivative), phytic acid, lipoic acid; lysophosphatidic acid, skin peel agents (e.g., phenol and the like), vitamin $B_3$ compounds and retinoids which enhance the keratinous tissue appearance benefits of the present disclosure, especially in regulating keratinous tissue condition, e.g., skin condition.

The cosmetic agents of the present disclosure may contain a safe and effective amount of a vitamin $B_3$ compound. Vitamin $B_3$ compounds are particularly useful for regulating skin conditions. When vitamin $B_3$ compounds are present in the cosmetic agents of the instant disclosure, the cosmetic agents preferably contain from about 0.01% to about 50%, more preferably from about 0.1% to about 10%, even more preferably from about 0.5% to about 10%, and still more preferably from about 1% to about 5%, still more preferably from about 2% to about 5%, by weight of the cosmetic agent, of the vitamin $B_3$ compound.

Exemplary derivatives of the foregoing vitamin $B_3$ compounds include nicotinic acid esters, including non-vasodilating esters of nicotinic acid (e.g., tocopheryl nicotinate), nicotinyl amino acids, nicotinyl alcohol esters of carboxylic acids, nicotinic acid N-oxide and niacinamide N-oxide. Examples of suitable vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.). The vitamin compounds may be included as the substantially pure material, or as an extract obtained by suitable physical and/or chemical isolation from natural (e.g., plant) sources.

The cosmetic agents of the present disclosure may also contain a retinoid. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$-$C_{22}$ alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. Nos. 4,677,120, issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell et al.; U.S. Pat. No. 5,124,356, issued Jun. 23, 1992 to Purcell et al.; and U.S. Pat. No. Reissue 34,075, issued Sep. 22, 1992 to Purcell et al. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). Preferred retinoids are retinol, retinyl palmitate, retinyl acetate, retinyl propionate, retinal and combinations thereof. The retinoid may be included as the substantially pure material, or as an extract obtained by suitable physical and/or chemical isolation from natural (e.g., plant) sources. The retinoid is preferably substantially pure, more preferably essentially pure. The cosmetic agents of this disclosure may contain a safe and effective amount of the retinoid, such that the resultant cosmetic agent is safe and effective for regulating keratinous tissue condition, preferably for regulating visible and/or tactile discontinuities in skin, more preferably for regulating signs of skin aging, even more preferably for regulating visible and/or tactile discontinuities in skin texture associated with skin aging. The cosmetic agents preferably contain from or about 0.005% to or about 2%, more preferably 0.01% to or about 2%, retinoid. Retinol is preferably used in an amount of from or about 0.01% to or about 0.15%; retinol esters are preferably used in an amount of from or about 0.01% to or about 2% (e.g., about 1%); retinoic acids are preferably used in an amount of from or about 0.01% to or about 0.25%; tocopheryl-retinoate, adapalene, and tazarotene are preferably used in an amount of from or about 0.01% to or about 2%.

Where the cosmetic agents of the present disclosure contain both a retinoid and a Vitamin $B_3$ compound, the retinoid is preferably used in the above amounts, and the vitamin B.sub.3 compound is preferably used in an amount of from or about 0.1% to or about 10%, more preferably from or about 2% to or about 5%.

The cosmetic agents of the present disclosure may contain a safe and effective amount of a Hydroxy Acid or hyaluronic acid or tannic acid. Preferred hydroxy acids for use in the cosmetic agents of the present disclosure include salicylic acid and salicylic acid derivatives. When present in the cosmetic agents of the present disclosure, hyaluronic or salicylic acid is preferably used in an amount of from about 0.01% to about 50%, more preferably from about 0.1% to about 20%, even more preferably from about 0.1% to about 10%, still more preferably from about 0.5% to about 5%, and still more preferably from about 0.5% to about 2%.

Peptides including but not limited to, di-, tri-, and tetra-peptides and derivatives thereof, may be included in the cosmetic agents of the present disclosure in amounts that are safe and effective. As used herein, "peptides" refers to both the naturally occurring peptides and synthesized peptides. Also, useful herein are naturally occurring and commercially available cosmetic agents that contain peptides.

Suitable dipeptides for use herein include Carnosine (beta-ala-his). Suitable tripeptides for use herein include, gly-his-lys, arg-lys-arg, his-gly-gly. Preferred tripeptides and derivatives thereof include palmitoyl-gly-his-lys, which may be purchased as Biopeptide CL.RTM. (100 ppm of palmitoyl-gly-his-lys commercially available from Sederma, France); Peptide CK (arg-lys-arg); Peptide CK+(ac-arg-lys-arg-NH.sub.2); and a copper derivative of his-gly-gly sold commercially as lamin, from Sigma (St. Louis, Mo.). Suitable tetrapeptides for use herein include Peptide E, arg-ser-arg-lys (SEQ ID NO: 1).

Further peptide is selected from palmitoyl-gly-his-lys, beta-ala-his, their derivatives, and combinations thereof. More preferably, the additional peptide is selected from palmitoyl-gly-his-lys, their derivatives, and combinations thereof.

When included in the present cosmetic agents, the peptides are preferably included in amounts of from about 0.000001% to about 10%, more preferably from about 0.000001% to about 0.1%, even more preferably from about 0.00001% to about 0.01%, by weight of the cosmetic agent. In certain embodiments which include the peptide, Carnosine.RTM., the cosmetic agents preferably contain from about 0.1% to about 5%, by weight of the cosmetic agent, of such peptides. In other embodiments wherein the peptide-containing cosmetic agent Biopeptide CL.RTM. is included, the resulting cosmetic agent preferably contains from about 0.1% to about 10%, by weight of the cosmetic agent, of the Biopeptide.

The cosmetic agents of the present disclosure may include a safe and effective amount of an anti-oxidant/radical scavenger. The anti-oxidant/radical scavenger is especially useful for providing protection against UV radiation which may cause increased scaling or texture changes in the stratum corneum and against other environmental agents which may cause skin damage.

A safe and effective amount of an anti-oxidant/radical scavenger may be added to the cosmetic agents of the subject disclosure, preferably from about 0.1% to about 10%, more preferably from about 1% to about 5%, of the cosmetic agent.

Anti-oxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethyl-chroman-2-carboxylic acid (commercially available under the tradename Trolox.RTM.), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, 1methionine, proline, superoxide dismutase, silymarin, tea extracts, grape skin/seed extracts, melanin, and rosemary extracts may be used. Preferred anti-oxidants/radical scavengers are selected from tocopherol sorbate and other esters of tocopherol, more preferably tocopherol sorbate. For example, the use of tocopherol sorbate in topical cosmetic agents and applicable to the present disclosure is described in U.S. Pat. No. 4,847,071, issued on Jul. 11, 1989 to Donald L. Bissett, Rodney D. Bush and Ranjit Chatterjee.

The cosmetic agents of the present disclosure may also contain a safe and effective amount of a chelator or chelating agent. As used herein, "chelator" or "chelating agent" means an active agent capable of removing a metal ion from a system by forming a complex so that the metal ion may not readily participate in or catalyze chemical reactions. The inclusion of a chelating agent is especially useful for providing protection against UV radiation which may contribute to excessive scaling or skin texture changes and against other environmental agents which may cause skin damage.

A safe and effective amount of a chelating agent may be added to the cosmetic agents of the subject disclosure, preferably from about 0.1% to about 10%, more preferably from about 1% to about 5%, of the cosmetic agent. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995. Preferred chelators useful in cosmetic agents are furildioxime, furilmonoxime, and derivatives thereof.

The cosmetic agents of the present disclosure may optionally contain a flavonoid compound. Flavonoids are broadly disclosed in U.S. Pat. Nos. 5,686,082 and 5,686,367, both of which are herein incorporated by reference. Flavonoids suitable for use in the present disclosure are flavanones selected from unsubstituted flavanones, mono-substituted flavanones, and mixtures thereof; chalcones selected from unsubstituted chalcones, mono-substituted chalcones, di-substituted chalcones, tri-substituted chalcones, and mixtures thereof; flavones selected from unsubstituted flavones, mono-substituted flavones, di-substituted flavones, and mixtures thereof; one or more isoflavones; coumarins selected from unsubstituted coumarins, mono-substituted coumarins, di-substituted coumarins, and mixtures thereof; chromones selected from unsubstituted chromones, mono-substituted chromones, di-substituted chromones, and mixtures thereof; one or more dicoumarols; one or more chromanones; one or more chromanols; isomers (e.g., cis/trans isomers) thereof; and mixtures thereof. By the term "substituted" as used herein means flavonoids wherein one or more hydrogen atom of the flavonoid has been independently replaced with hydroxyl, C1-C8 alkyl, C1-C4 alkoxyl, O-glycoside, and the like or a mixture of these substituents. Examples of suitable flavonoids include, but are not limited to, unsubstituted flavanone, mono-hydroxy flavanones (e.g., 2-hydroxy flavanone, 6-hydroxy flavanone, 7-hydroxy flavanone, etc.), mono-alkoxy flavanones (e.g., 5-methoxy flavanone, 6-methoxy flavanone, 7-methoxy flavanone, 4-methoxy flavanone, etc.), unsubstituted chalcone (especially unsubstituted trans-chalcone), mono-hydroxy chalcones (e.g., 2-hydroxy chalcone, 4-hydroxy chalcone, etc.), di-hydroxy chalcones (e.g., 2,4-dihydroxy chalcone, 2,4-dihydroxy chalcone, 2,2-dihydroxy chalcone, 2,3-dihydroxy chalcone, 2,5-dihydroxy chalcone, etc.), and tri-hydroxy chalcones (e.g., 2,3,4-trihydroxy chalcone, 4,2,4-trihydroxy chalcone, 2,2,4-trihydroxy chalcone, etc.), unsubstituted flavone, 7,2-dihydroxy flavone, 3,4-dihydroxy naphthoflavone, 4-hydroxy flavone, 5,6-benzoflavone, and 7,8-benzoflavone, unsubstituted isoflavone, daidzein (7,4-dihydroxy isoflavone), 5,7-dihydroxy-4-methoxy isoflavone, soy isoflavones (a mixture extracted from soy), unsubstituted coumarin, 4-hydroxy coumarin, 7-hydroxy coumarin, 6-hydroxy-4-methyl coumarin, unsubstituted chromone, 3-formyl chromone, 3-formyl-6-isopropyl chromone, unsubstituted dicoumarol, unsubstituted chromanone, unsubstituted chromanol, and mixtures thereof.

They may be synthetic materials or obtained as extracts from natural sources (e.g., plants). The naturally sourced material may also further be derivatized (e.g., an ester or ether derivative prepared following extraction from a natural source). Flavonoid compounds useful herein are commercially available from a number of sources, e.g., Indofine Chemical Company, Inc. (Somerville, N.J.), Steraloids, Inc. (Wilton, N.H.), and Aldrich Chemical Company, Inc. (Milwaukee, Wis.). Mixtures of the above flavonoid compounds may also be used.

A safe and effective amount of an anti-inflammatory agent may be added to the cosmetic agents of the present disclosure, preferably from about 0.1% to about 10%, more preferably from about 0.5% to about 5%, of the cosmetic agent. The anti-inflammatory agent enhances the skin appearance benefits of the present disclosure, e.g., such agents contribute to a more uniform and acceptable skin tone or color. The exact amount of anti-inflammatory agent to be used in the cosmetic agents will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone. A second class of anti-inflammatory agents which is useful in the cosmetic agents includes the non-steroidal anti-inflammatory agents. The variety of compounds encompassed by this group are well-known to those skilled in the art. For detailed disclosure of the chemical structure, synthesis, side effects, etc. of non-steroidal anti-inflammatory agents, one may refer to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology, 1, R. A. Scherrer, et al., Academic Press, New York (1974).

The cosmetic agents of the present disclosure may also contain a safe and effective amount of an anti-cellulite agent. Suitable agents may include, but are not limited to, xanthine compounds (e.g., caffeine, tannine, theophylline, theobromine, and aminophylline).

The cosmetic agents of the present disclosure may also contain a safe and effective amount of a topical anesthetic. Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

The cosmetic agents of the present disclosure may contain a tanning active. When present, it is preferable that the cosmetic agents contain from about 0.1% to about 20%, more preferably from about 2% to about 7%, and still more preferably from about 3% to about 6%, by weight of the cosmetic agent, of dihydroxyacetone as an artificial tanning active. Dihydroxyacetone, which is also known as DHA or 1,3-dihydroxy-2-propanone, is a white to off-white, crystalline powder.

The compound may exist as a mixture of monomers and dimers, with the dimers predominating in the solid crystalline state. Upon heating or melting, the dimers break down to yield the monomers. This conversion of the dimeric form to the monomeric form also occurs in aqueous solution. Dihydroxyacetone is also known to be more stable at acidic pH values. See, The Merck Index, Tenth Edition, entry 3167, p. 463 (1983), and "Dihydroxyacetone for Cosmetics", E. Merck Technical Bulletin, 03-304 110, 319 897, 180 588.

The cosmetic agents of the present disclosure may contain a skin lightening agent. When used, the cosmetic agents preferably contain from about 0.1% to about 10%, more preferably from about 0.2% to about 5%, also preferably from about 0.5% to about 2%, by weight of the cosmetic agent, of a skin lightening agent. Suitable skin lightening agents include those known in the art, including kojic acid, arbutin, ascorbic acid and derivatives thereof (e.g., magnesium ascorbyl phosphate or sodium ascorbyl phosphate), and extracts (e.g., mulberry extract, placental extract). Skin lightening agents suitable for use herein also include those described in the PCT publication No. 95/34280, in the name of Hillebrand, corresponding to PCT Application No. U.S. Ser. No. 95/07432, filed Jun. 12, 1995; and co-pending U.S. application Ser. No. 08/390,152 filed in the names of Kvalnes, Mitchell A. DeLong, Barton J. Bradbury, Curtis B. Motley, and John D. Carter, corresponding to PCT Publication Ser. No. 95/23780, published Sep. 8, 1995.

Further examples of such suitable lightening materials include, but are not limited to, ascorbyl glucosides, vitamin C, retinol and retinol derivatives, water soluble licorice extracts, bearberry extracts, *Rumex crispus* extracts, milk proteins including hydrolyzed milk proteins, N,N,S-tris(carboxymethyl)cysteamines, oleanolic acids, *perilla* oils, placenta extract, Saxifragia *sarmentosa*, grape extract, Azadirachta indica A. Juss. Var., *Glycyrrhiza glabra* Linn., *Morinda citrifolia* Linn., Naringi *crenulata* (Roxb) Nicolson, *Ligusticum* chiangxiong Hort., Asmunda *japonica* Thumb., *Stellaria medica* (L.) cyr., Sedum sarmentosum Bunge, *Ligusticum* lucidum Ait., *Ilex purpurea* Hassk, Emblica, apigenin, ascorbyl palmitol, carruba polyphenol, hesperitin, hydroquinone, inabata polyphenol, isoliquirtigenin, kaempherol-7-neohesperidose, L-mimosine, luteolin, oil-soluble licorice extract, oxa acid, phenyl isothiocyanate, silymarin, T4CA, tetrahydro curcumin, unitrienol, ursolic-oleanolic acid, UVA/URSI, N,N,S-tris(carboxymethyl) cysteamine, cococin, TDPA, carboxycysteamine, cococin, *perilla* seed extract, *perilla* extract, juniperic acid, stenolama chusana (L.) ching, or any combinations thereof.

Cosmetic agents of the present disclosure may comprise a skin soothing or skin healing active. Skin soothing or skin healing actives suitable for use herein include panthenoic acid derivatives (including panthenol, dexpanthenol, ethyl panthenol), aloe vera, allantoin, bisabolol, and dipotassium glycyrrhizinate. A safe and effective amount of a skin soothing or skin healing active may be added to the present cosmetic agent, preferably, from about 0.1% to about 30%, more preferably from about 0.5% to about 20%, still more preferably from about 0.5% to about 10%, by weight of the cosmetic agent formed. The topical cosmetic agents of the present disclosure may also contain a safe and effective amount of bisabolol. Bisabolol is a naturally occurring unsaturated monocyclic terpene alcohol.

It is the primary active component of chamomile extract/oil. Bisabolol may be synthetic (d,1-alpha-isomer or (+/−)-alpha-isomer) or natural ((−)-alpha-isomer) in origin and may be used as essentially pure compounds or mixtures of compounds (e.g., extracts from natural sources such as chamomile). The alpha form of bisabolol (a-bisabolol) is used in a variety of cosmetic products as a skin conditioning or soothing agent. As used herein, "bisabolol" includes chamomile extract or oil and any isomers and tautomers of such. Suitable bisabolol compounds are commercially available as a natural material from Dragoco (Totowa, N.J.) under the product name alpha-bisabolol natural and as a synthetic material from Fluka (Milwaukee, Wis.) under the product name alpha-bisabolol. In the cosmetic agents of the present disclosure, the cosmetic agent preferably contains from about 0.001% to about 50%, by weight of the cosmetic agent, more preferably from about 0.01% to about 20%, even more preferably from about 0.01% to about 15%, and still more preferably from about 0.1% to about 10%, of bisabolol, even more preferably from about 0.1% to about 5%.

The cosmetic agents of the present disclosure may contain naturally occurring molecules. Such actives are capable of acting as anti-inflammatory agents, skin lightening agents, skin brightening agents, skin smoothing/healing agents, cleansing agents, etc. They may be naturally sourced or synthetically derived. The naturally sourced material may also further be derivatized (e.g., an ester or ether derivative prepared following extraction from a natural source). All forms, including salts are considered within the scope of the present disclosure. For example, molecules including or obtained from moringa extract, olive oil or olive extracts, grape vine, including resveratrol mon, di and/or tri glycolates, plant and fruit extracts may be included in the cosmetic agent. When used, the cosmetic agents preferably contain from about 0.00001% to about 10%, more preferably from about 0.2% to about 5%, also preferably from about 0.5% to about 2%, by weight of the cosmetic agent.

The cosmetic agents of the present disclosure may contain an antimicrobial or antifungal active. Such actives are capable of destroying microbes, preventing the development of microbes or preventing the pathogenic action of microbes. A safe and effective amount of an antimicrobial or antifungal active may be added to the present cosmetic agents, preferably, from about 0.0001% to about 10%, more preferably from about 0.01% to about 5%, and still more preferably from about 0.05% to about 2%.

Examples of antimicrobial and antifungal actives include .beta.-lactam drugs, quinolone drugs, ciprofloxacin, norfloxacin, tetracycline, erythromycin, amikacin, 2,4,4-trichloro-2-hydroxy diphenyl ether, 3,4,4-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, zinc pyrithione and clotrimazole.

Preferred examples of actives useful herein include those selected from salicylic acid, benzoyl peroxide, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2-hydroxy diphenyl ether, 3,4,4'-trichlorocarbanilide, octopirox, lidocaine hydrochloride, clotrimazole, miconazole, ketoconazole, neocycin sulfate, and mixtures thereof.

Exposure to ultraviolet light may result in excessive scaling and texture changes of the stratum corneum. Therefore, the cosmetic agents of the subject disclosure may optionally contain a sunscreen active. As used herein, "sunscreen active" includes both sunscreen agents and physical sunblocks. Suitable sunscreen actives may be organic or inorganic.

Inorganic sunscreens useful herein include the following metallic oxides: titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof. When used herein, the inorganic sunscreens are present in the amount of from about 0.1% to about 20%, preferably from about 0.5% to about 10%, more preferably from about 1% to about 5%, by weight of the cosmetic agent.

A wide variety of conventional organic sunscreen actives are suitable for use herein. Sagarin, et al., at Chapter VIII, pages 189 et seq., of Cosmetics Science and Technology (1972), discloses numerous suitable actives. Specific suitable sunscreen actives include, for example: p-aminobenzoic acid, its salts and its derivatives (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzone, sulisobenzone, dioxybenzone, benzoresorcinol, 2,2,4,4-tetrahydroxybenzophenone, 2,2-dihydroxy-4,4'-dimethoxybenzophenone, octabenzone; 4-isopropyldibenzoylmethane; butyl-methoxydibenzoylmethane; etocrylene; octocrylene; [3-(4'-methylbenzylidene boman-2-one), terephthalylidene dicamphor sulfonic acid and 4-isopropyl-di-benzoylmethane. Of these, 2-ethylhexyl-p-methoxycinnamate (commercially available as PARSOL MCX), 4,4-t-butyl methoxydibenzoyl-methane (commercially available as PARSOL 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxy-propyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene and mixtures of these compounds, are preferred.

More preferred organic sunscreen actives useful in the cosmetic agents useful in the subject disclosure are 2-ethylhexyl-p-methoxycinnamate, butylmethoxydibenzoyl-methane, 2-hydroxy-4-methoxybenzo-phenone, 2-phenyl-benzimidazole-5-sulfonic acid, octyldimethyl-p-aminobenzoicacid, octocrylene and mixtures thereof.

Also, particularly useful in the cosmetic agents are sunscreen actives such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991. The sun screening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sun screening agents are 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methyl-aminobenzoic acid ester with 4-hydroxydibenzoylmethane; 4-N, N-(2-ethylhexyl)methyl-aminobenzoic acid ester of 2-hydroxy-4-(2-hydroxyethoxy) benzophenone; 4-N,N-(2-ethylhexyl)-methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethyl-hexyl)-4-aminobenzoic acid ester of 4-(2-hydroxyethoxy) dibenzoylmethane and mixtures thereof. Especially preferred sunscreen actives include 4,4'-t-butyl-methoxydibenzoylmethane, 2-ethylhexyl-p-methoxycinnamate, phenyl benzimidazole sulfonic acid, and octocrylene. A safe and effective amount of the organic sunscreen active is used, typically from about 1% to about 20%, more typically from about 2% to about 10% by weight of the cosmetic agent. Exact amounts will vary depending upon the sunscreen or sunscreens chosen and the desired Sun Protection Factor (SPF).

The cosmetic agents of the present disclosure may contain a conditioning agent selected from humectants, moisturizers, or skin conditioners. A variety of these materials may be employed, and each may be present at a level of from about 0.01% to about 20%, more preferably from about 0.1% to about 10%, and still more preferably from about 0.5% to about 7% by weight of the cosmetic agent. These materials include, but are not limited to, guanidine, urea, glycolic acid and glycolate salts (e.g., ammonium and quaternary alkyl ammonium), salicylic acid, lactic acid and lactate salts (e.g., ammonium and quaternary alkyl ammonium), aloe vera in any of its variety of forms (e.g., aloe vera gel); polyhydroxy alcohols such as sorbitol, mannitol, xylitol, erythritol, glycerol, hexanetriol, butanetriol, propylene glycol, butylene glycol, hexylene glycol and the like; polyethylene glycols; sugars (e.g., melibiose) and starches; sugar and starch derivatives (e.g., alkoxylated glucose, fructose, glucosamine); hyaluronic acid; lactamide monoethanolamine; acetamide monoethanolamine; panthenol; allantoin; and mixtures thereof. Also, useful herein are the propoxylated glycerols described in U.S. Pat. No. 4,976,953, to Orr et al, issued Dec. 11, 1990.

Also useful are various $C_1$-$C_{30}$ monoesters and polyesters of sugars and related materials. These esters are derived from a sugar or polyol moiety and one or more carboxylic acid moieties. Such ester materials are further described in, U.S. Pat. Nos. 2,831,854, 4,005,196, to Jandacek, issued Jan. 25, 1977; U.S. Pat. No. 4,005,195, to Jandacek, issued Jan. 25, 1977, U.S. Pat. No. 5,306,516, to Letton et al, issued Apr. 26, 1994; U.S. Pat. No. 5,306,515, to Letton et al, issued Apr. 26, 1994; U.S. Pat. No. 5,305, 514, to Letton et al, issued Apr. 26, 1994; U.S. Pat. No. 4,797,300, to Jandacek et al, issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985.

Preferably, the conditioning agent is selected from urea, guanidine, sucrose polyester, panthenol, dexpanthenol, allantoin, and combinations thereof.

In addition, the topical cosmetic agent may contain conventional cosmetic adjuvants and additives such as preservatives, antioxidants, fatty substances, oils, water, organic solvents, silicones, thickeners, emollients, emulsifiers, sunscreens, defoamers, a surfactant, a filler, a sequestering agent, an anionic, a cationic, a nonionic or an amphoteric polymer or a mixture thereof, a propellant, an acidifying agent or a basic agent, a dye, a colorant/coloring agent, an abrasive, a skin sensate, an astringent, a pigment or a nano pigment, or any other ingredient typically formulated in cosmetic compositions. Such cosmetic ingredients which are suitable for use in the composition of the present disclosure and which are conventionally used in the skin care industry are described in, for example, the CTFA Cosmetic Ingredient Handbook, Second Edition (1992), but are not limited thereto.

The cosmetic agents of the present disclosure, without limiting, may be present in form of lotions, milky lotions, creams and oil, oil in emulsions, watery substances, gels, hydrogels, shampoos, hair rinses, hair conditioners, hair creams, hair dyes, hair colors, pre- or post-treatment agents for hair dyeing and coating agents for split hair, etc.

The formulation type of the cosmetic agents of the present disclosure may be of any type, including solution system, soluble system, emulsion system, gel system, powder dispersing system or water-oil two phase system.

While particular embodiments of the present disclosure have been illustrated and described, it would be obvious to those skilled in the art that various other changes and modifications may be made without departing from scope of the disclosure. It is therefore intended to cover in the appended claims all such changes and modifications and all such changes and/or modifications are considered to be within the scope of the present disclosure described herein.

What is claimed is:

1. A method of applying one or more cosmetic products by using a cosmetic pad housed in a moisture barrier bag layer, comprising:
    opening the moisture barrier bag layer; wherein the moisture barrier bag layer blocks moisture and air from the cosmetic pad; wherein the cosmetic pad comprises:
        a top layer constructed of non-woven material,
        a bottom layer configured to allow for ventilation through the bottom layer,
        at least one heating element between the top layer and the bottom layer,
        a finger pocket in between the top layer and the bottom layer, and
        a formulation layer comprising at least one formulation-top layer, at least one formulation-bottom layer, and the one or more cosmetic products in between the formulation-top layer and the formulation-bottom layer;
        wherein the formulation layer is between the top layer and the bottom layer;
    wherein the at least one heating element activates upon opening the moisture barrier bag layer;
    inserting one or more fingers into the finger pocket,
    releasing the one or more cosmetic products housed in the formulation layer, and
    applying the cosmetic pad on the skin.

2. The method of claim 1, wherein the step of applying the one or more cosmetic products comprises attaching the cosmetic pad to a device or an applicator.

3. The method of claim 1, wherein the cosmetic pad further comprises an air-diffusing layer in between the top layer and the bottom layer.

4. The method of claim 1, wherein the bottom layer comprises one or more apertures for ventilation.

5. The method of claim 1, wherein the bottom layer comprises a breathable material for ventilation.

6. The method of claim 1, wherein at least one heating element is a single-phase heating element.

7. The method of claim 1, wherein at least one heating element is a dual-phase heating element.

8. The method of claim 1, wherein the formulation layer is between the top layer and the at least one heating element.

9. The method of claim 1, wherein the formulation-top layer and the formulation-bottom layer are impregnated with the one or more cosmetic products.

10. The method of claim 1, wherein the at least one heating element comprises a heating layer between a breathable heating-top layer and a breathable heating-bottom layer.

* * * * *